(12) United States Patent
Yang et al.

(10) Patent No.: US 7,422,568 B2
(45) Date of Patent: Sep. 9, 2008

(54) DEVICE, SYSTEMS AND METHODS FOR LOCALIZED HEATING OF A VESSEL AND/OR IN COMBINATION WITH MR/NMR IMAGING OF THE VESSEL AND SURROUNDING TISSUE

(75) Inventors: Xiaoming Yang, Baltimore, MD (US); Ergin Atalar, Columbia, MD (US); Christopher Yeung, Pikesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 13 days.

(21) Appl. No.: 10/404,903

(22) Filed: Apr. 1, 2003

(65) Prior Publication Data

US 2004/0024434 A1 Feb. 5, 2004

Related U.S. Application Data

(60) Provisional application No. 60/369,241, filed on Apr. 1, 2002.

(51) Int. Cl.
*A61M 31/00* (2006.01)
(52) U.S. Cl. .................................. 604/93.01; 606/191
(58) Field of Classification Search ............... 604/93.01, 604/96.01, 507, 19–22, 48, 95.01; 606/213, 606/191–194, 198
See application file for complete search history.

(56) References Cited

U.S. PATENT DOCUMENTS

| | | | |
|---|---|---|---|
| 5,178,618 A | 1/1993 | Kandarpa | 606/28 |
| 5,498,238 A * | 3/1996 | Shapland et al. | 604/501 |
| 5,702,384 A | 12/1997 | Umeyama et al. | 604/892.1 |
| 5,810,767 A | 9/1998 | Klein | |
| 5,921,954 A * | 7/1999 | Mohr et al. | 604/508 |
| 6,004,269 A | 12/1999 | Crowley et al. | 600/439 |
| 6,028,066 A | 2/2000 | Unger | |

(Continued)

OTHER PUBLICATIONS

Jean-Michel Serfaty, MD, et al. "Toward MRI-Guided Coronary Catheterization: Visualization of Guiding Catheters, Guidewires, and Anatomy in Real Time", Journal of Magnetic Resonance Imaging, 12:590-594 (2000).

(Continued)

*Primary Examiner*—Roy D. Gibson
*Assistant Examiner*—Aaron Roane
(74) *Attorney, Agent, or Firm*—Peter F. Corless; William J. Daley, Jr.; Edwards Angell Palmer & Dodge LLP

(57) ABSTRACT

Featured are devices, systems and methods for localized heating of a vessel as well as devices, systems and methods for MR/NMR imaging of a vessel while locally heating a portion of the vessel. More particularly featured are such devices, systems and methods for use when administering or delivering therapeutic agents including genes and/or drugs to the tissues of the vessel. Such a method includes positioning a thermal energy delivery device proximal a target site with the vessel of a body and activating the thermal energy delivery device so as to heat the target site thereby locally increasing a temperature of tissue at the target site. In further embodiments, the method includes introducing a therapeutic medium to the target site over a predetermined time period, and wherein said activating occurs at least one of before, during or after said step of introducing.

33 Claims, 7 Drawing Sheets

U.S. PATENT DOCUMENTS

| | | | |
|---|---|---|---|
| 6,066,123 | A | 5/2000 | Li et al. |
| 6,113,629 | A * | 9/2000 | Ken .......................... 623/1.1 |
| 6,162,796 | A | 12/2000 | Kaplitt et al. |
| 6,193,685 | B1 | 2/2001 | Goodin |
| 6,232,295 | B1 | 5/2001 | Kayyem et al. |
| 6,398,757 | B1 * | 6/2002 | Varenne et al. ........ 604/103.02 |

OTHER PUBLICATIONS

Stephen J. Dodd, et al. "Detection of Single Mammalian Cells by High-Resolution Magnetic Resonance Imaging", Biophysical Journal, Jan. 1999, p. 103-109, vol. 76, No. 1.

S. Du, et al., Intravascular MR Imaging/RF Heating-Enhanced Vascular Gene Transduction: An In Vivo Feasibility Study, Annual Meeting of International Society of Magnetic Resonance in Medicine (May 10-17, 2002).

Serfaty, et al. Magnetic Resonance in Medicine 49:258-263 (2003).

Qiu, et al., Journal Of Magnetic Resonance Imaging 16:716-720 (2002).

Yeung, et al., Magnetic Resonance in Medicine 48:1096-1098 (2002).

Serfaty, et al. Journal of Magnetic Resonance Imaging 12:590-594 (2000).

Dodd, et al., Biophys Journal, p. 103-109, vol. 76, No. 1 (Jan. 1999).

* cited by examiner

DEVICE, SYSTEMS AND METHODS FOR LOCALIZED HEATING OF A VESSEL AND/OR IN COMBINATION WITH MR/NMR IMAGING OF THE VESSEL AND SURROUNDING TISSUE

This application claims the benefit of U.S. Provisional Application Serial No. 60/369,241 filed Apr. 1, 2002, the teachings of which are incorporated herein by reference in their entirety.

FIELD OF INVENTION

The present invention relates to devices, systems and methods for localized heating of a vessel as well as devices, systems and methods for MR/NMR imaging of a vessel while locally heating a portion of the vessel, more particularly such devices, systems and methods for use when administering or delivering a therapeutic medium including genes and/or drugs to the tissues of the vessel, and more specifically to such devices, systems and methods when the vessel is more specifically a part of the vascular system of a body (e.g., a blood vessel).

BACKGROUND OF THE INVENTION

Atherosclerotic cardiovascular disease remains the leading cause of mortality in the United States (see, e.g., *American Heart Association*, 1999 *Heart And Stroke Statistical Update*, Dallas, Tex., American Heart Association). Gene therapy is a rapidly expanding field with great potential for the treatment of atherosclerotic cardiovascular diseases as well as diseases involving other organs or parts of a mammalian body (e.g., human body) in which therapeutic agents can be delivered to a targeted site of a vessel lumen. Several genes, such as vascular endothelial growth factor (VEGF), have been shown to be useful for preventing acute thrombosis, blocking post-angioplasty restenosis, and stimulating growth of new blood vessels (angiogenesis) (Nabel, 1995, *Circulation* 91: 541-548; Isner, 1999, *Hosp. Pract.* 34: 69-74).

In the early days of vascular gene therapy, many investigators were searching for the ideal vector, one that would allow efficient transduction and long-term stable transgene expression in target cells, including: (i) viral vectors, such as retroviral (Miller A. Retroviral vectors. Curr Top Microbiol Immunol 1992; 158:1-24), adenoviral (Kozarsky K, Wilson J. Gene therapy: adenovirus vectors (Review). Curr Opin genet Dev 1993; 3:499-503), and adeno-associated viral vectors (Muzyczka N. Use of adeno-associated virus as a general transduction vector for mammalian cells. Curr Top Microbiol Immunol 1992; 158:97-129); and (ii) nonviral vectors, such as DNA and RNA vectors (Wolff J, Maline R, Williams P. Direct gene transfer into mouse muscle in vivo. Science 1990; 247:1465-1468), synthetic oligonucleotides (Stein C, Cheng Y. Antisense oligonucleotides as therapeutic agents—is the bullet really magical? Science 1993; 261:1004-1012), and liposomes (Felgner P, Gadek T, Holm M. Lipofection: A highly efficient, lipid-mediated DNA-transfection procedure. Proc Natl Acad Sci USA 1987; 84:7413-7417). None of these types of vectors, however, were found to be ideal for both efficient gene transfection and stable gene expression. For example, plasmid DNA has a number of advantages as a gene therapy vector, including (a) easy construction, (b) no need for an infectious agent, (c) long-term transgene expression, and (d) no immune responses. Plasmid DNA, however, suffers a prominent disadvantage because of the relatively low efficiency of transduction in vivo.

Another challenge to vascular gene therapy is the ability to deliver therapeutic genes to the target site. Different gene delivery techniques have been developed, including: ex vivo gene delivery, such as endovascular stents seeded with genetically modified endothelial cells which are then reimplanted into the target vessel, surgically-based delivery, which involves directly injecting genes into surgically-isolated target vessels; percutaneous delivery, which involves the direct administration of genes into the target through a percutaneous approach; and catheter-based delivery (Thomas J, Kuo M, Chawla M, et al. Vascular gene therapy. RadioGraphics 1998; 18:1373-1394). Of these gene delivery techniques, catheter-based delivery seems to hold the most promise for vascular applications.

Catheter-based gene delivery has some prominent advantages over other gene delivery methods, including (a) precise gene delivery to a specific anatomic location, (b) minimal morbidity, (c) no unwanted systemic effects, and (d) the ability to combine with conventional interventions, such as angioplasty and endovascular stent placement. Since 1990, several catheters have been tested as vector delivery systems, including double-balloon catheters [Goldman, Atherosclerosis #154], porous and microporous infusion catheters (Wolinsky H, Thung S. Use of a perforated balloon catheter to deliver concentrated heparin into the wall of the normal canine artery. J Am Coll Cardiol 1990; 15:475-481), hydrogel catheters (Fram D, Aretz T, Azrin M. Localized intramural drug delivery during balloon angioplasty using hydrogel-coated balloons and pressure-augmented diffusion. J Am Coll Cardiol 1994; 23:1570-1577), and dispatch catheters (Tahlil O, Brami M, Feldman L, Branellec D, Steg P. The Dispatch catheter as a delivery tool for arterial gene transfer. Cardiovasc Res 1997; 33:181-187). However, gene transfer with these delivery catheters is currently performed under x-ray fluoroscopy, which displays, using a contrast medium, only the lumen of the vessel without providing direct imaging information about the vessel wall or atherosclerotic plaques. Therefore, one cannot properly monitor either the interaction between the genes and the atherosclerotic lesion or the existence and the concentration of the genes in the target lesion during and after gene delivery.

As such, efficient gene transfection into a target-specific cell is one of the challenges for vascular gene therapy in cardiovascular disease. Several studies have shown that gene transfection and expression can be significantly enhanced one- to four-fold with heating, which has been tested in different cells, such as prostate tumor cells, chondrocytes, kidney cells, and arterial SMCs (Blackburn R, Galoforo S, Corry P, Lee Y. Adenoviral-mediated transfer of a heat-inducible double suicide gene into prostate carcinoma cells. Cancer Research 1998; 58:1358-1362; Greenleaf W, Bolander M, Sarkar G, Goldring M, Greenleaf J. Artificial cavitation nuclei significantly enhance acoustically induced cell transfection. Ultrasound in medicine & Biology 1998; 24:p587-595; Yang, et al. Unpublished data). Moreover, the incorporation of DNA with adjuvants or heat-sensitive promoters may further enhance gene transfection and expression under heating. Proposed mechanisms for heat-enhancement of gene transfection may include heating efforts that cause tissue fracture, increased permeability of the plasma membrane and cell metabolism, and increase the activity of heat-sensitive heat shock proteins. In clinical practice, however, it is not feasible to heat the entire body to temperatures (e.g., increase bulk body temperature by 4 deg) that have been shown to enhance transfection and expression. As such, the challenge now faced is how to place an internal heating source within the body to generate heat only in a local heating region at the target site rather than through the entire body. In addition, the challenge also posed is to provide such local heating in a fashion so as to allow for in vivo monitoring of the target site and surrounding tissue and so as to be effective in enhancing the delivery/administering of the gene for therapy.

It thus would be desirable to provide a new device, systems and methods for localized heating of a target site of a vessel, such as for example, the endothelial tissues of a blood vessel to facilitate the administration or delivery of a therapeutic medium to the target site. It would be particularly desirable to provide such a device, system and method that also would allow for MR/NMR imaging of the tissues at, about and proximal the target site while administering or delivering the therapeutic medium to the target site and while locally heating the tissues of the target site. It also would be particularly desirable to provide such devices, systems and methods that can allow a flow of fluid to be maintained within the vessel while performing any of localized heating, administering/delivering the therapeutic medium and MR/NMR imaging of the tissues at and proximal the target site.

SUMMARY OF THE INVENTION

According to one aspect, the present invention features devices, systems and methods for locally thermally heating a target site of a vessel or vessel lumen so as to thereby enhance the delivery or administering of a therapeutic medium to tissues of the target site. According to other aspects of the present invention, such devices, systems and methods are such that thermal heating can be performed while MR/NMR imaging of the tissues at and about or proximal the target site of the vessel. In more particular embodiments, the volume of the vessel being heated is different from the volume that is being MR/NMR imaged. More specifically, the volume being imaged is typically greater than the volume being heated. In an exemplary embodiment, the vessel is a blood vessel of a mammalian body (e.g., human body) and the tissues of the target site comprise the endothelial tissues or the wall of the blood vessel being targeted.

In other embodiments, such local thermal heating of the target site of the vessel lumen includes thermally heating the target site at least one of before, during or after administering/delivering the therapeutic medium to the target site. In further embodiments, such thermal heating is performed during one of (i) before and during administering/delivering the therapeutic medium; (ii) during and after administering/delivering the therapeutic medium; (iii) before and after administering/delivering the therapeutic medium; or (iv) before, during, and after administering/delivering the therapeutic medium.

According to a more particular aspect of the present there is featured a method for delivering a therapeutic medium to a target site of a vessel lumen that includes the steps of positioning a thermal energy delivery device proximal the target site; introducing the therapeutic medium to the target site, more particularly the tissues of the target site, over a time period; and activating the thermal energy delivery device so as to supply thermal energy to the target site thereby locally increasing the temperature of the tissues at the target site. The activation of the thermal energy device is controlled so that said activating occurs at least one of before, during or after said step of introducing the therapeutic medium. In further embodiments, the activation of the thermal energy delivery device is controlled so that said activating occurs during one of (i) before and during administering/delivering the therapeutic medium; (ii) during and after administering/delivering the therapeutic medium; (iii) before and after administering/ delivering the therapeutic medium; or (iv) before, during, and after administering/delivering the therapeutic medium.

In a particular embodiment, said positioning includes providing a catheter in which is housed the thermal energy delivery device; introducing the catheter into the vessel lumen and manipulating the catheter within the vessel lumen so the catheter is positioned proximal the target site. In a further particular embodiment, the catheter being provided includes a balloon member and said positioning further includes inflating the balloon member when the catheter is proximal the target site so as to position the thermal energy delivery device at a desired location with respect to the target site. In another particular embodiment, said inflating locates the thermal energy device so as to be located proximal or at the centerline of the vessel lumen.

In further embodiments, the method further comprises providing a power source that is operably coupled to the thermal energy delivery device and wherein said activating further includes controlling operation of the power source so as to selectively activate the thermal energy delivery device when delivery of thermal energy is desired. In yet further embodiments, the method further comprises providing a control mechanism operably coupled to the power source that controls the activation of the power source and so as to thereby control an amount of thermal energy; a duration of application of the thermal energy being delivered to the tissue of the target site; and when the thermal energy is to be delivered to the tissue of the target site.

In yet further embodiments, the provided catheter is configured and arranged so as to include a guide wire, where a portion of the guide wire comprises the thermal energy delivery device, which guide wire is operably coupled to the power source. In more particular embodiments, the power source comprises an RF generator that is operably and electrically coupled to the guide wire that supplies RF signals to the guide wire so as to output thermal energy from the portion of the wire comprising the thermal energy delivery device. In further particular embodiments, the method includes providing a control mechanism that is operably coupled to the RF generator so as to control application of RF signals to the guide wire for the generation of thermal energy therefrom to the target site.

In yet further embodiments, the method further includes introducing the catheter into the vessel lumen and manipulating it within the vessel lumen while the balloon member is in a deflated condition and inflating the balloon member after determining that the catheter is positioned proximal the target site. In particular embodiments, the thermal energy delivery device, or more particularly the portion of the guide wire comprising the thermal energy delivery devices is disposed within the balloon member such that when the balloon member is inflated the thermal energy delivery device or that related portion of the guide wire is at the desired location with respect to the target site, for example at or proximal the centerline of the vessel lumen.

According to another aspect of the present invention, such a method further includes the step of MR/NMR imaging tissues at, about and/or proximal the target site, at least while activating the thermal energy delivery device and more particularly also at least while administering/delivering the therapeutic medium tto the target site tissues. In further embodiments, the provided guide wire is configured and arranged so as to form a MR receiver antenna which detects MR/NMR signals from the tissues at, about and/or proximal the target site. In yet further embodiments, the method includes providing an MR/NMR receiving apparatus as is known to those skilled in the art that is operably coupled to the MR receiver antenna. The MR/NMR receiving apparatus is configured and arranged as is known to those skilled in that art so as to receive and process the MR/NMR signals from the MR receiver antenna and to provide outputs therefrom that are used to develop images of the volume at, about or proximal the target site being MR/NMR scanned.

In yet further embodiments, the method includes providing a filtering mechanism operably coupled between each of (i) the power source and the guide wire/MR receiver antenna and (ii) the NR/NMR receiving apparatus and the guide wire/MR receiver antenna for selectively filtering signals communicable therebetween. In particular embodiments, the filtering mechanism operably coupled between the MR/NMR receiving apparatus and the guide wire/MR receiver antenna is configured and arranged so signals emanating from the power source/RF generator comprising the power source or signals having a frequency less than a first predetermined frequency, are not inputted into the MR/NMR receiving apparatus. Similarly the filtering mechanism disposed between the power source/the RF generator comprising the power source is configured and arranged so as to pass signals having a frequency greater than a second predetermined frequency. In yet further particular embodiments, the MR/NMR signals are at a frequency that is different from the frequency of the signals emanating from the power source/RF generator comprising the power source.

Consequently, MR/NMR images can be provided that image the delivery of the therapeutic medium to the target tissue including when thermal energy is being supplied to the target site. In this way, a single device can be introduced into the vessel lumen and positioned proximal the target site thereof which device is capable of providing thermal energy to the target site to facilitate delivery/administration of the therapeutic medium and which also can be used to MR/NMR image the tissues at, about and/or proximal the target site. More specifically, the guide wire can be used to manipulate the catheter so it is positioned proximal the target site, to deliver heat energy to the target site and to MR/NMR image the tissues at, about and/or proximal the target site. Such MR/NMR imaging provides a mechanism by which delivery or administration of the therapeutic medium and its movement within the tissues at the target site can be imaged and tracked. In further specific embodiments, the therapeutic medium is configured and arranged so as to include a MR/NMR contrast agent to facilitate MR/NMR imaging of the therapeutic agent.

As indicated above, also featured are systems and devices that embody and carry out the above-described methodology of the present invention.

Other aspects and embodiments of the invention are discussed below.

Definitions

The instant invention is most clearly understood with reference to the following definitions:

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" or "including" is intended to mean that the compositions, methods, devices, apparatuses and systems include the recited elements, but do not exclude other elements. "Consisting essentially of", when used to define compositions, devices, apparatuses, systems, and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients, elements and substantial method steps. Embodiments defined by each of these transition terms are within the scope of this invention.

As used herein, a "target cell" or "recipient cell" refers to an individual cell or cell which is desired to be, or has been, a recipient of exogenous nucleic acid molecules, polynucleotides and/or proteins. The term is also intended to include progeny of a single cell, and the progeny may not necessarily be completely identical (in morphology or in genomic or total DNA complement) to the original parent cell due to natural, accidental, or deliberate mutation. A target cell may be in contact with other cells (e.g., as in a tissue) or may be found circulating within the body of an organism. As used herein, a "target cell" is generally distinguished from a "host cell" in that a target cell is one which is found in a tissue, organ, and/or multicellular organism, while as host cell is one which generally grows in suspension or as a layer on a surface of a culture container.

As used herein, a "subject" is a vertebrate, preferably a mammal, more preferably a human. Mammals include, but are not limited to, murines, simians, humans, farm animals, sport animals, and pets.

The terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancerspecific antigens in a sample obtainable from a patient.

As used herein, a "composition" refers to the combination of an active agent (e.g., such as a therapeutic agent, nucleic acid vector) with a contrast agent. The composition additionally can comprise a pharmaceutically acceptable carrier or excipient and/or one or more accessory molecules which may be suitable for diagnostic or therapeutic use in vitro or in vivo. The term "pharmaceutically acceptable carrier" as used herein encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see *Martin Remington's Pharm. Sci.,* 15th Ed. (Mack Publ. Co., Easton (1975)).

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 1:
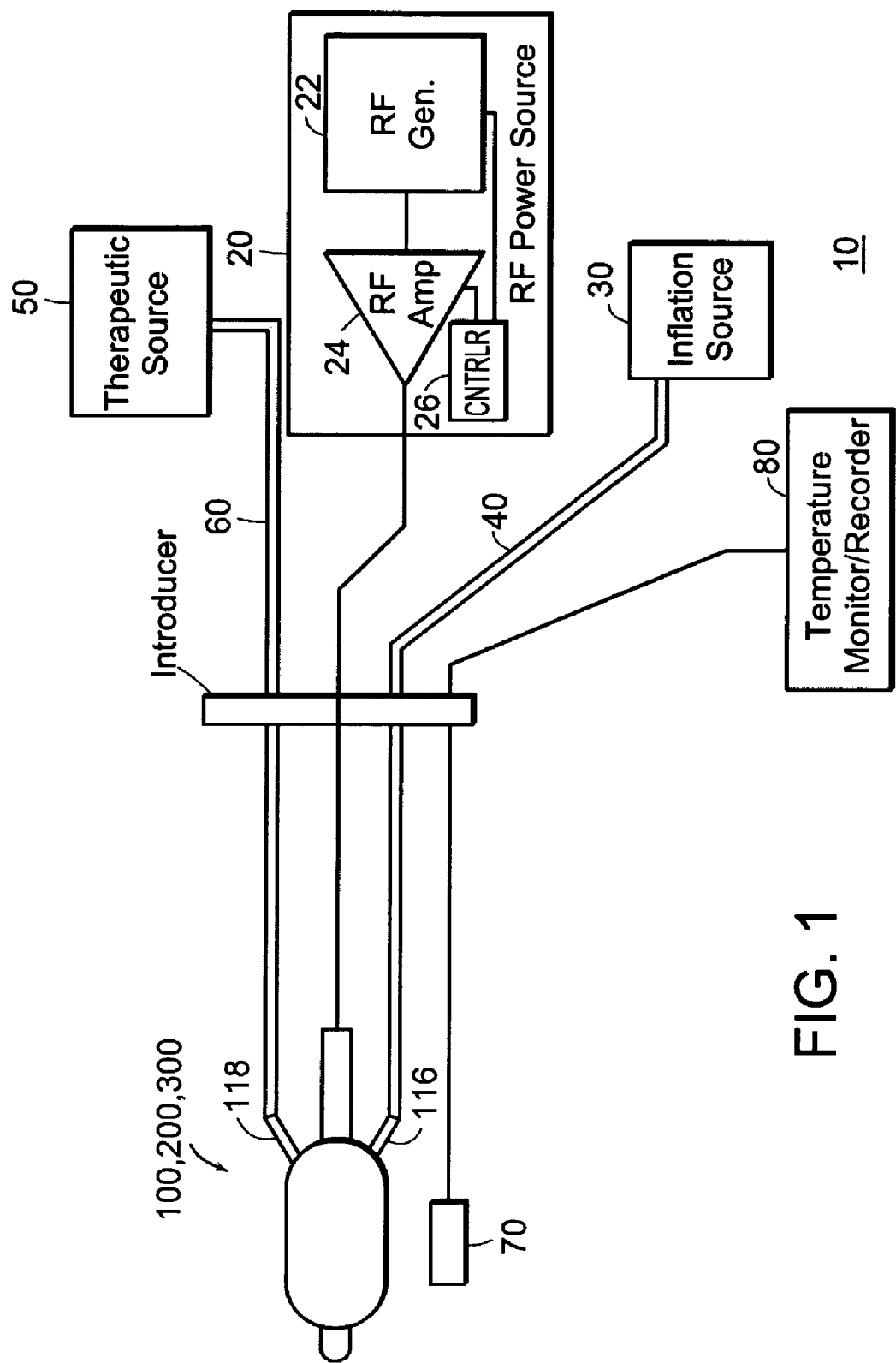
FIG. 1 is a block diagram of a catheter system according to one aspect of the present invention.
Figure 4:
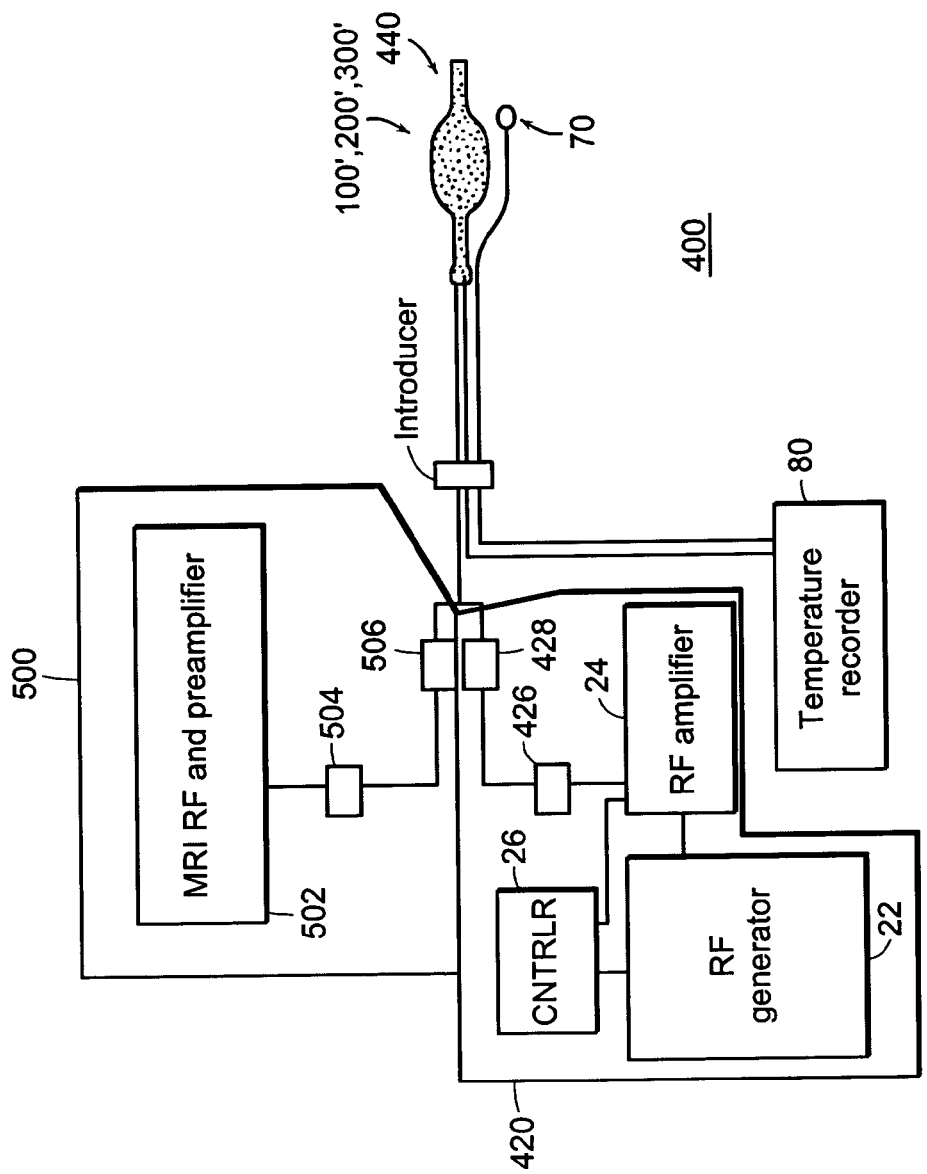
FIG. 4 is a block diagram of a catheter system according to another aspect of the present invention.

Referring now to the various figures of the drawing wherein like reference characters refer to like parts, there is shown in FIG. 1 a block diagram of a catheter system 10 according to one aspect of the present invention that includes that capability of performing any of a number of discrete functions or capabilities alone, in combination and/or collectively. Such functions or capabilities, which are described further hereinafter, include: delivering therapeutic compositions/agents to the tissues of a target site of a lumen or body cavity (e.g., target cells); manipulating the therapeutic delivery device 100 of catheter system so it is positioned proximal the target site, localizing the therapeutic delivery device to the target site, and delivering thermal or heat energy to the tissues of the target site including the target cells. In addition, there is shown in FIG. 4 a block diagram of a catheter system 400 according to another aspect of the present invention, that includes that capability of performing, alone, in combination and/or collectively, any of the discrete functions or capabilities described above as well as MR/NMR imaging of the tissues at, about and/or proximal the target site more particularly performing such imaging using a MR/NMR receiver antenna that is disposed within the lumen or body cavity proximal the target site. As also further described hereinafter, this catheter system is more particularly adaptable and capable of delivering heat energy to the target tissues while also performing such MR/NMR imaging of the tissues at, about and/or proximal the target site.

It also should be recognized that while the following discussion may describe the systems, method and devices of the present invention with respect to the administration and/or delivery of therapeutic agents/compositions to the target site or wall of a blood vessel of the vascular of a human, this shall not be construed as limiting the present invention to that specific application. It is contemplated and considered as being within the scope of the present invention, for the catheter systems 10, 400 of the present invention as well as related device and methods of the present invention to be adapted for use so as to deliver therapeutic agents/compositions to any tissues of a human or other mammalian body that can be accessed using a therapeutic delivery device of the present invention via a lumen, vessel lumen, cavity or the like that exists within such body. Such tissues or target cells include, but are not limited to, cells of the heart, the vascular system, liver, prostrate, breasts, kidneys, brain, thyroid, and muscles as well as tissues/cells of sinuses, esophagus, ear canal and air passages. For example, it is contemplated that the catheter systems 10, 400 of the present invention can be adapted for use along with known colonoscopy procedures so therapeutic compositions/agents could be delivered to the intestinal tract and/or colon of the body.

It also should be recognized that the methods or techniques for navigating or manipulating catheters or delivery devices such as those of the present invention, including methods and techniques for inserting such catheters or delivery devices into a lumen, vessel lumen, body cavity or blood vessel of a body, are well known to those skilled in the art and thus are not explicitly recited in their entirety herein. An example of methods for navigating catheters to desired target locations as is known in the art are described in, for example, Rutherford, *Vascular Surgery*, P edition (Saunders Co 1989).

The catheter system 10 as shown in FIG. 1 includes a RF power source 20, an inflation source 30, a therapeutic source 50, a therapeutic agent delivery device 100 and tubing 40, 60 that fluidly couples the therapeutic delivery device to each of the inflation source and the therapeutic source. In further embodiments, such a catheter system 10 further includes a thermoprobe or temperature sensor 70 and a temperature monitoring/recording device 80.

Figure 2:
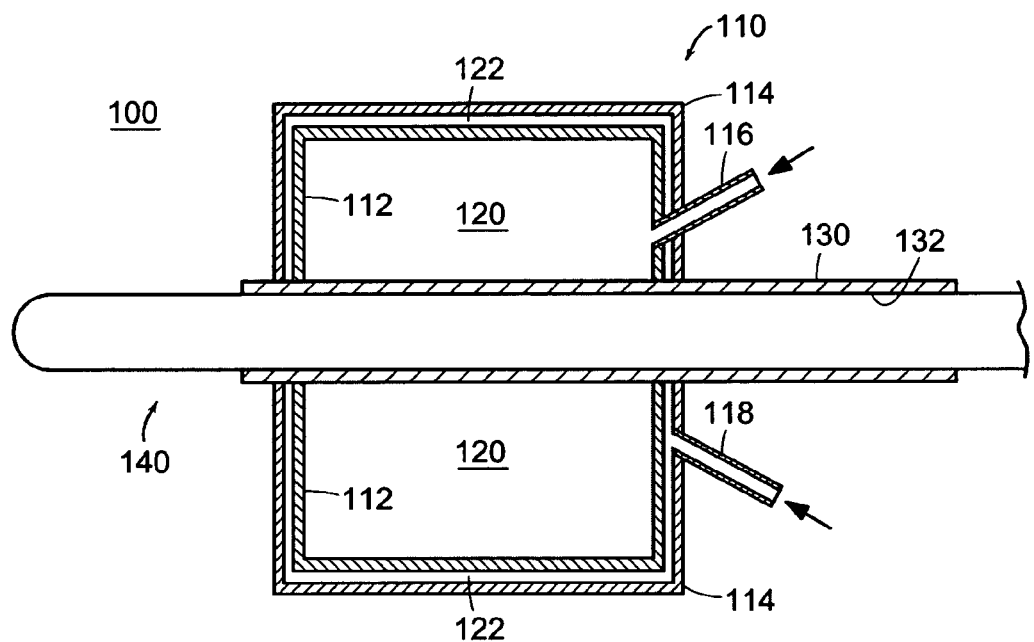
FIG. 2 is a cross-section view of a therapeutic delivery device according to an embodiment of the present invention.
Figure 3:
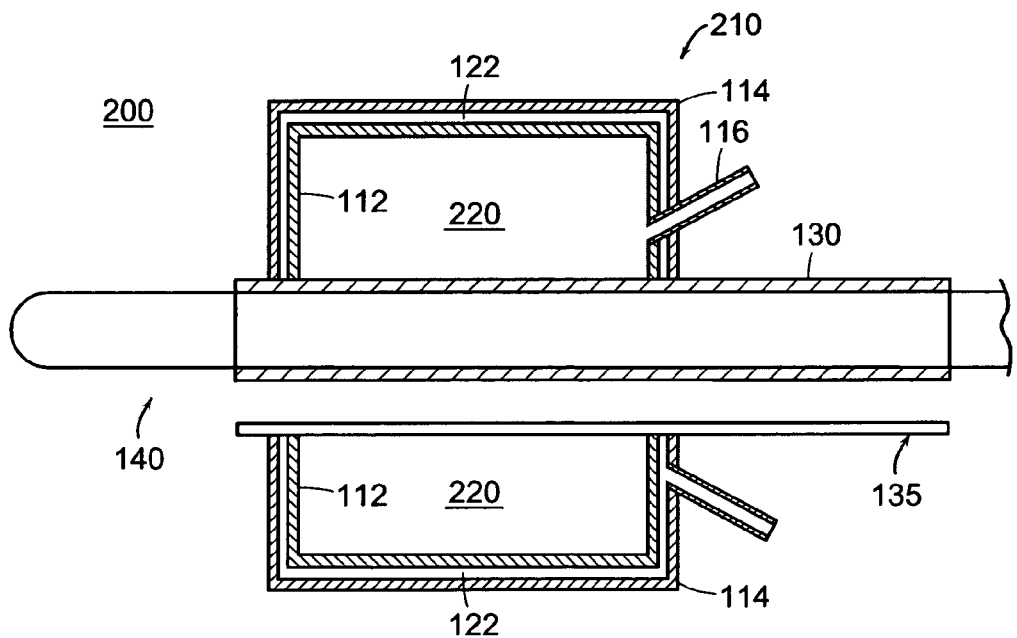
FIG. 3 is a cross-section view of a therapeutic delivery device according to a further embodiment of the present invention.

Referring now to FIGS. 2-3, which show cross-sectional views of exemplary therapeutic delivery devices 100, 200 according to the present invention that includes that capability of performing any of a number of discrete functions or capabilities including delivering therapeutic compositions/agents to the tissues of a target site of a vessel lumen (e.g.; target cells), delivering thermal or heat energy to the tissues of the target site, and, for the therapeutic delivery device 200 shown in FIG. 3, MR/NMR imaging of the tissues at, about and/or proximal the target site more particularly performing such imaging using a MR/NMR receiver antenna that is disposed within the vessel lumen proximal the target site. As also further described hereinafter, such a therapeutic delivery device 200 is more particularly adaptable and capable of delivering heat energy to the target tissues while also performing such MR/NMR imaging of the tissues at, about and/ or proximal the target site. It should be recognized that while a porous or perfusion type of balloon catheter is illustrated and described hereinafter for purposes of describing the therapeutic delivery devices 100, 200 of the present invention it should be recognized that the catheter systems 10, 400 of the present invention are adaptable for use with any of a number of other types of catheters or delivery devices as is known to those skilled in the art including those used in connection with interventional vascular procedures such as angiographic catheters or embolization catheters including other therapeutic delivery devices described herein.

It also should be recognized that while a porous or perfusion type of balloon catheter is illustrated and described hereinafter for purposes of describing the catheter systems of the present invention it should be recognized that the catheter system of the present invention is adaptable for use with any of a number of other types of catheters as is known to those skilled in the art including those used in connection with interventional vascular procedures such as angiographic catheters, or embolization catheters. Also, and while the following discussion may describe the systems, method and devices of the present invention with respect to the insertion and delivery of therapeutic agents/compositions to the target site or wall of a blood vessel of the vascular of a human, this shall not be construed as limiting the present invention to that application. It is contemplated and considered as being within the scope of the present invention, for the catheter systems of the present invention as well as related device and methods of the present invention to be adapted for use so as to deliver therapeutic agents to any tissues of the human or other mammalian body that can be accessed by means of an existing lumen, vessel lumen or cavity of the body. Such tissues or target cells include, but are not limited to, cells of the heart, the vascular system, liver, prostrate, breasts, kidneys, brain, thyroid, muscles, sinuses and air passages. For example, it contemplated that the catheter system of the present invention could be adapted for use in conjunction with known colonoscopy procedures so therapeutic compositions/agents could be delivered to the intestinal tract and/or colon of the body.

Now referring to FIG. 2, there is shown a therapeutic delivery device 100 according to one embodiment of the present invention for delivering therapeutic agents/compositions and heat energy to the tissues or target cells of a target site of a vessel, vessel lumen, lumen, blood vessel or body cavity. Although reference hereinafter may be to one or more of a lumen, vessel lumen, body cavity or blood vessel it shall be understood that such reference is not intended to be limiting as to the scope of the functional capabilities of the therapeutic devices of the present invention as it is within the scope of the present invention, as hereinabove described, that the delivery devices and catheter systems of the present invention to be adapted for use in wide range of applications where the tissues or cells of the body being targeted can be accessed or reached via the use of a delivery device of the present invention. Such a therapeutic delivery device 100 includes a housing 110 and a heating guide wire 140.

The delivery device housing 110 is re-configurable from a first, deflated or reduced cross-section state (not shown) to a second expanded, inflated or increased cross-section state. In the first state, the housing 110 is substantially tubular along it length and has a size or cross-section that allows the housing to be inserted into the body as well as the vessel lumen or body cavity and manipulated/navigated therein so the housing is positioned proximal the target site. It should be recognized, however, that other shapes and configurations appropriate for the insertion and manipulation/navigation of the housing 110 in a given application are contemplated for use and are considered within the scope of the present invention.

In a particular embodiment, the housing comprises a balloon member 112, a flexible porous outer member 114 that is disposed generally about the balloon member and a channel member 130. The balloon member 112 may also be referred to as an angioplasty balloon or a dilation balloon by those skilled in the art as the balloon member 112 of the present invention in use is generally expanded outwardly to contact and occlude a portion of the lumen, body cavity or blood vessel the housing is disposed in for a given application as is illustrated for example in FIGS. 6-8. When the housing is in the first state, the balloon member 112 is deflated so the flexible outer member 114 and the balloon member are compressed about a channel member 130 to provide the desired shape and cross-section for insertion and navigation/manipulation.

In an illustrated embodiment, the flexible outer member 114 is shown as extending about the entire outer surface of the balloon member 112. It is within the scope of the present invention, however, for the flexible outer member 114 to be configured and arranged so as to extend at least about those portions of the balloon member 112 outer surface such that the flexible outer member contacts the tissues of the target site when the balloon member is in its second, expanded or inflated state.

The housing channel member 130 extends generally lengthwise within the housing 110. The channel member 130 includes a through aperture, channel or lumen 132 that also extends generally lengthwise to the housing 110. The delivery device guide wire 140 also is received within the channel member lumen 132, and in particular embodiments, the guide wire extends through the channel member lumen and extends outwardly from a distal end of the housing. The balloon member 112 also is connected to the channel member 118 so as to define a volume or first region 120 there between. Similarly, the flexible outer member 114 is secured to the channel member 130 and/or also to the balloon member 112 so as to generally define another volume or second region 122 that is substantially between the flexible outer member and the balloon member.

It should be recognized that the balloon member 112 and the flexible member 114 are well known elements to those skilled in the art of balloons that are used in medical access devices and, thus, although described and shown with reference to a particular embodiments herein, the general features (e.g. size, shape, materials) of the balloon member 112 and/or flexible member 114 may be in accordance with conventional balloons. For example, and as known to those skilled in the art, the exact dimensions of the balloon member 112 and flexible member 114 should be configured to the type of lumen/vessel/cavity being accessed by the therapeutic delivery device 100 of the present invention. In a particular exemplary preferred embodiment, the balloon member 112 and the flexible member 114 are made of a biocompatible, distendable material that is capable of being inflated to a size sufficient to compress a target lumen's walls. Such biocompatible, distendable materials include, but are not limited to, flexible medical-grade silicone rubber or polyethylene terepthalate (PET).

Similarly, the channel member 130 should be made of a of a biocompatible material that is appropriate for use with the materials being used for the balloon member 112 and the flexible member 114 as well as being appropriate for the intended use. Such biocompatible materials include, but arenot limited to, flexible medical-grade silicone rubber or polyethylene terepthalate (PET). It should be recognized that the size and shape of the channel member 130 are based on the type of lumen/vessel/cavity being accessed by the therapeutic delivery device 100 of the present invention. It also should be recognized that the size and shape of the axially extending lumen 132 of the channel member 130 are based on the size and shape of the guide wire 140 being received therein. In more particular embodiments, the axially extending lumen shall have a cross-section or size such that the housing 110 remains secured to the guide wire while manipulating the guide wire 140 during insertion of the therapeutic delivery device type into the lumen/vessel/cavity being accessed by the therapeutic delivery device 100.

The balloon member 112 also is configured to include an input port 116, which input port includes an axial extending lumen that is in fluid communication with the delivery device first region 120. As illustrated in FIG. 1, the balloon member input port 116 is coupled, fluidly coupled to tubing 40, which in turn is fluidly coupled to the inflation source 30. Thus, and in this fashion, the delivery device first region 120 is fluidly coupled to the inflation source 30. In use, and is known to those skilled in the art, the inflation source 30 selectively supplies an inflation medium to the delivery device first region 120 so as to cause the balloon member 112 to inflate and expand outwardly from the channel member 130. Typically, the inflation source 30 includes a mechanism for selectively pumping or otherwise moving the inflation medium at a pressure sufficient to inflate the balloon member 112 as well as to maintain the balloon member in an inflated condition during the procedure. In an illustrative embodiment, such a mechanism comprises an infusion pump (e.g., such as the Harvard Apparatus, Holliston, Mass.). The inflating medium is any of a number of mediums known to those skilled in the art that is appropriate for the intended use and includes for example a saline solution (i.e., warm saline solution) for vascular applications or a gas when the lumen or body cavity is a gaseous environment.

The flexible outer member 114 preferably is a porous member, and in particular embodiments includes a plurality or more of microholes therein. In this way, and as known to those skilled in the art, a therapeutic medium such as a therapeutic composition/agent disposed within the delivery device second region 122 and under pressure traverses the microholes and is dispersed or delivered to the tissues or the like of the vessel lumen/body cavity that the surface of the flexible outer member 114 is in contact with. The term "microhole" implies no particular limitation on size. In one particular embodiment, a plurality of linearly-arrayed, 15-25 µm microholes are disposed on at least one lateral surface of the flexible outer member 114 that is in contact with the tissues or the like of the vessel lumen/body cavity. It also is within the scope of the present invention for the surface(s) of the flexible member 114 that come into contact with the tissues of the target site to be configured and arranged with surface artifacts, such as needles or other penetrating elements, that enhance of otherwise facilitate the infusion of the therapeutic medium to such tissues or target cells.

The flexible outer member 114 also is configured to include an input port 118, which input port includes an axial extending lumen that is in fluid communication with the delivery device second region 122. As illustrated in FIG. 1, the flexible member input port 118 is coupled, fluidly coupled to tubing 60, which in turn is fluidly coupled to the therapeutic agent/composition source 50. Thus, and in this fashion, the second region 122 is fluidly coupled to the source 50 of the therapeutic composition/agent to be administered/delivered to the cells or tissues of the target site. The particulars of the therapeutic medium including the therapeutic composition(s) or therapeutic agent(s) that can comprise such a therapeutic medium that can be administered/delivered to the target site tissues or cells are described hereinafter.

In use, and is known to those skilled in the art, the therapeutic source 50 selectively supplies a therapeutic medium comprising a therapeutic composition or agent to the delivery device second region 122 under a pressure sufficient to cause this therapeutic medium to pass through the plurality of microholes of the flexible outer member 114 and thus be dispersed to the tissues at the target site. The supplying of this therapeutic medium to the second region 122 also may cause the flexible outer member 114 to inflate and expand outwardly from the channel member 130. Typically, the therapeutic source 50 includes a mechanism for selectively pumping or otherwise moving the therapeutic medium at a pressure sufficient to cause the delivery of the medium to the target site tissues. In an illustrative embodiment, such a mechanism comprises an infusion pump (e.g., such as the Harvard Apparatus, Holliston, Mass.).

During vascular interventional procedures, the inflation of the balloon member 112 along with the flexible outer member 114 may cause intimal tears and subintimal dissection (see, e.g., Zollikofer, et al., 1992, In *Interventional Radiology*, W. Castaneda-Zuniga and S. Tadavarthy, Editors, Williams & Wilkins: Baltimore, Md., pp. 249-297). This is exploited in the design of the porous flexible member 114 that essentially directly injects the therapeutic medium from the therapeutic source 50 to these areas. Also, and in the case of MR/NMR imaging of these areas, the effects of balloon member inflation "injury" and accumulation of the contrast agents at these areas results in contrast enhancement of the target vessel wall, which is visualized during high-resolution MRI.

The flexible tubing 40, 60 is any of a number of biocomaptable tubing materials known to those skilled in the art that are appropriate for the intended use. In particular exemplary embodiments, the tubing 40, 60 is of the size and material of the tubing that is used for interventional vascular procedures.

The heating guide wire 140 of the present invention is any of a number of guide wires known to those skilled in the art including guide wires that are used in connection with interventional vascular procedures that are capable of generating heating energy therefrom when coupled to a power source. In more particular embodiments, the heating guide wire 140 is any of a number of known MR imaging guide wires that comprises a soft conducting tip wire that is an extended inner conductor from a coaxial cable. In exemplary embodiments, the guide wire is about 100-120 cm in length, where the conducting tip is about 4 cm in length and 0.4 mm in diameter and the remainder of the coaxial cable is about 96-116 cm in length and about 0.6 mm in diameter. In further exemplary embodiments, the inner conductor of the coaxial cable comprising the heating guide wire 140 according to the present invention is a gold-plated nitinol wire, the dielectric is polytetrafluoroethylene and the outer conductor comprises nitinol, more particularly the outer conductor is a nitinol tube with a copper coating on the inner surface thereof. It should be recognized that foregoing is merely illustrative and exemplary of a few dimensions and constructions of a heating guide wire 140 of the present invention and that other sizes, shapes, constructions, materials for such heating guide wires are contemplated for use with the present invention.

As illustrated in FIG. 1, the heating guide wire 140 is coupled; more particularly coupled electrically to an RF power source 20 that includes an RF generator 22 and an RF amplifier 24. The RF generator 22 is any of a number of devices known to those skilled in the art that can generate an RF signal having a given frequency (e.g., center frequency with a given bandwidth) and power output. Similarly, the RF amplifier 24 is any of a number of amplilfiers or devices known to those skilled in the art that can amplify, more particularly selectively amplify, such an RF signal having a given frequency and power output, and to output the inputted RF signal at a higher power output. Preferably, such RF amplifier 24 amplifies the input RF signal without introducing an un-acceptable amount of noise. In further embodiments, and as illustrated in FIG. 4, the RF power source 20 further includes matching/tuning and coupling circuitry, as is known to those skilled in the RF and MR imaging arts, that couples the heating guide-wire 140 to the RF power source, more particularly the output of the RF amplifier 24. It also should be recognized that other RF power amplification circuits as known to those skilled in the art, such as feedback type of circuits are contemplated for use with the present invention and are considered within the scope of the present invention.

In particular embodiments, the RF generator 22 is configured and arranged so as to provide a RF signal output having a frequency greater than 1 GHz, more particularly a frequency greater than 2 GHz, yet more particularly a frequency in the range of 2 GHz≦freq≦3 GHz, more specifically a frequency of about 3 GHz. In preferred embodiments, particularly when MR/NMR imaging of the tissue at, about and/or proximal the target site is to be conducted, the RF generator 22 is configured and arranged so the RF signals being inputted into the heating guide wire 140 are separated significantly from the MR/NMR signals being detected as well as the RF signals outputted in conjunction with such MR/NMR imaging processes. In exemplary embodiments, the RF generator 22 is configured and arranged so the RF signals inputted into the heating guide wire 140 are one of separated from the frequencies of the signals associated with the MR/NMR imaging process by one-at least 800 MHZ or is at a frequency that is about at least 3 times or more (e.g., 5 times) greater than the frequencies of the signals associated with the MR/NMR imaging process. In a specific exemplary embodiment, the RF generator 22 is a sinusoidal RF generator (e.g., Model PTS160, Programmed Test Sources, Littleton, Mass.), operating at 3 GHz, and the RF amplifier 224 is an RF power amplifier (e.g., Model 100L, EM, Rochester, N.Y.).

In further embodiments, the RF power source 20 is configured and arranged so as to selectively output RF signals to the heating guide wire 140 so that thermal or heating energy is controllably applied to the tissues of the target site. In more particular embodiments, the RF power source 20 includes a controller 26, or the catheter system 10 further includes a controller that is coupled to the RF power source 20, said controller being configured and arranged so as to selective control the signal outputs (e.g., turn the outputs on and off) from the RF power source. In further particular embodiments, the controller 20 also is configured and arranged so as to control the RF power source 20, more particularly the RF amplifier 24, so as to adjust and control the power amplitude or output of the outputted RF signals using any of a number of techniques known to those skilled in the art. In this way, the duration and timing of the application of the heating or thermal energy to the target site can be controlled as well so as to be optimal for administration or delivery of the therapeutic medium and so the amount of heating or thermal energy being applied can be controlled to optimize the temperature for delivery of the therapeutic medium as well as controlling the temperature to minimize adverse effect to the target site tissues.

As indicated above, there is shown in FIG. 3 a therapeutic delivery device 200 according to another embodiment of the present invention which therapeutic delivery device includes a housing 210 and a heating guide wire 140. The housing 210 comprises a balloon member 112, a flexible porous outer member 114 that is disposed generally about the balloon member, a channel member 130 and one or more perfusion channels 135. Reference shall be made to the heating guide wire 140, the balloon member 112, the flexible outer member 114, the input ports 116, 118 for the balloon member and the flexible outer member, the second channel 122, the channel member 130 and the heating guide wire.

The one or more perfusion channels 135 are arranged so as to extend lengthwise within the housing 110. Each of the one or more perfusion channels 135 are configured so as to include a through aperture, channel or lumen therein that also extends generally lengthwise to the housing 110 and so as to be open at both the distal and proximal ends of the housing. The lumen in each of the one or more perfusion channels 135 thus allows a biological fluid, such as blood, in the cavity/lumen/vessel being accessed that is otherwise blocked by the therapeutic device 200, to flow through the delivery device via the one or more perfusion channels. In this way, the administration or delivery of the therapeutic medium as well as heating of the tissues at the target site can be done without interruption that would be occasioned by temporary deflation of the balloon member or other action to temporarily re-establish flow of the biological fluid in the cavity/lumen/vessel being accessed. In more particular embodiments, the housing includes a plurality of perfusion channels 135 and the lumen for each of the one or more, or the plurality of, perfusion channels 135 is about 100 to about 500 μm in diameter.

In this delivery device embodiment, the balloon member 112 also is connected to the channel member 118 and the one or more perfusion channels 135 so as to define a volume or first region 220 there between. Reference shall be made to the foregoing discussion regarding the delivery device first region 120 as shown in FIG. 2 for further details of the first region 220 of FIG. 3.

As indicated above, in further embodiments of the catheter system 100 shown in FIG. 1, such a system includes a thermoprobe or temperature sensor 70 and a temperature monitoring device 80 operably coupled thereto electrical or optically depending upon the particulars of the temperature sensing device being used. In particular embodiments the temperature sensor 70 is a fiber-optic temperatures sensor (e.g., FISO Technologies, Ste-Foy, Quebec, Canada) or a fiber-optic temperature probe (Luxtron Cooperation, Santa Clara, Calif.). In a more particular exemplary embodiment, two fiber-optic temperature probes are run in parallel where one temperature probe is disposed proximal to or fixed onto the tip of the heating guide wire 140 and another is disposed between the surface of the flexible outer member 114 and the inner surface of the target wall of the lumen or body cavity. This ensures direct contact of the probe with the inner vessel wall during inflation of the balloon member 112.

In lieu of direct measurement of temperature, and in an alternative embodiment, temperature images are developed using known MR/NMR thermometry techniques. MR thermometry is used to create temperature mapping, which describes the location and distribution of RF heating in the tissues being imaged. MR temperature imaging is performed using an ECG-gated, segmented k-space spoiled gradient echo (SPGR) pulse sequence, which allows phase difference maps to be reconstructed. In this technique, an initial baseline MR image is taken to calculate temperature changes in subsequent maps. The data is typically processed during data acquisition by a program written on ADW (Advantage Window Workstation, GE) to construct temperature maps and from these maps, the RF heating region is identified. Real-time temperature maps can be used to maintain the local heating region at an elevated temperature of from between, for example 1-11° C.

In yet further embodiments, the housing 110, 210, is configured and arranged so as to include a one or more channels to receive therein one or more optical fibers (not shown), to aid in imaging of the body cavity/lumen/vessel. For example, the optical fiber(s) can be used to receive fluorescent light from cells that have incorporated a vector comprising a fluorescent reporter gene as described above. The optical fibers also can be used to monitor the navigation of the device itself. To this latter end, the surface of the housing 110, 210 (e.g., surface closer to the walls of the body cavity/lumen/vessel) may be marked with one or more radio-opaque markers. In still other embodiments, a channel may be provided for accepting an ultrasonic probe for providing treatment to a target tissue in the form of ultrasound, this can be used to complement the therapeutic medium delivery treatment methods.

Referring now to FIG. 4, there is shown a catheter system 400 according to another aspect of the present invention, which catheter system is more particularly configured and arranged so as to be capable of using the therapeutic delivery device according to the present invention to MR/NMR image the tissues at, about or proximal the target site. Such a catheter system 400 includes a RF power source 420, a therapeutic medium delivery device 100', 200', 300' that includes a housing 110 and a MR/NMR imaging and heating (MRIH) guide wire 440. In further embodiments, the catheter system 10 further includes a thermoprobe or temperature sensor 70 and a temperature monitoring/recording device 80. Although not specifically shown in FIG. 4, such a catheter system 400 also includes an inflation source 30, a therapeutic source 50 and tubing 40, 60 that fluidly couples the therapeutic delivery device 100', 200', 300' to each of the inflation source and the therapeutic source. In further embodiments, such a catheter system 10 further includes a thermoprobe or temperature sensor 70 and a temperature monitoring/recording device 80. As to the elements, features or structure having reference numerals in common with FIGS. 1-3, reference shall be made to the discussion above regarding these figures for details and description not otherwise provide below. For purposes of better describing the catheter system 400 according to this embodiment of the present invention, the illustration of the catheter system also includes a portion of the MR/NMR receiving subsystem 500 of a MR/NMR imaging system that would be connected thereto.

According to this embodiment, the therapeutic delivery device 100, 200 includes a MR/NMR imaging and heating [MRIH] guide wire 440 according to the present invention. More particularly, the MRIH guide wire 440 is in the form of a loopless MR/NMR receiver antenna as is known to those skilled in the art, more particularly loopless MR/NMR receiver antennas that are used in connection with interventional vascular procedures. In more particular embodiments, the MRIH guide wire 440 is any of a number of known MR imaging guide wires that comprises a soft conducting tip wire that is an extended inner conductor from a coaxial cable. In exemplary embodiments, the MRIH guide wire 440 is about 100-120 cm in length, where the conducting tip is about 4 cm in length and 0.4 mm in diameter and the remainder of the coaxial cable is about 96-116 cm in length and about 0.6 mm in diameter. In further exemplary embodiments, the inner conductor of the coaxial cable comprising the MRIH guide wire 440 according to the present invention is a gold-plated nitinol wire, the dielectric is polytetrafluoroethylene and the outer conductor comprises nitinol, more particularly the outer conductor is a nitinol tube with a copper coating on the inner surface thereof. It should be recognized that foregoing is merely illustrative and exemplary of a few dimensions and constructions of a MRIH guide wire 440 of the present invention and that other sizes, shapes, constructions, materials for such heating guide wires are contemplated for use with the present invention.

As illustrated in FIG. 4, the MRIH guide wire 440 is coupled; more particularly coupled electrically to an RF power source 420 and to the MR/NMR receiving subsystem 500 of a MR/NMR imaging system. The RF power source includes an RF generator 22, an RF amplifier, matching/tuning and coupling circuitry 426, a filter 428 and a controller 26. As indicated above reference shall be made to the foregoing discussion regarding the RF generator 22 and the RF amplifier 24 as well as the foregoing discussion regarding the controller 26 thereof for further details regarding the operation and characteristics of these functional components of the RF power source. The matching/tuning and coupling circuitry 426 is any of a number of circuits/circuit arrangements known to those skilled in the RF and MR/NMR arts that are appropriate for the intended application.

The power source filter 428 is any of a filtering number of mechanisms known to those skilled in the RF and MR/NMR arts, that allows frequencies above a predetermined frequency to pass therethrough and blocks the transmission of frequencies that are less than the predetermined frequency and in more specific embodiments, the filter 428 is a high pass type of filter. In preferred embodiments, the predetermined frequency for the filter 428 is established so the RF signals being inputted into the MRIH guide wire 440 are separated significantly from the MR/NMR signals being detected as well as the RF signals outputted in conjunction with such MR/NMR imaging processes. In addition, the predetermined frequency is established such that any noise that may be generated by the RF generator 22 or during signal amplification by the RF amplifier 24 is separated significantly from the MR/NMR signals being detected as well as the RF signals outputted in conjunction with such MR/NMR imaging processes.

In exemplary embodiments, the filter 428 is configured and arranged so the RF signals inputted into the MRIH wire 440 are one of separated from the frequencies of the signals associated with the MR/NMR imaging process by one at least 800 MHZ or is at a frequency that is about at least 3 times or more (e.g., 5 times) greater than the frequencies of the signals associated with the MR/NMR imaging process. In particular exemplary embodiments, the RF power source filter 428 is configured and arranged so as to pass RF signals having a frequency greater than 1 GHz, more particularly a frequency greater than 2 GHz, yet more particularly a frequency in the range of 2 GHz$\leq$freq$\leq$3 GHz, more specifically a frequency of about 3 GHz.

In this way, even in the case where the RF generator 22 is configured so as to generate RF signals at a frequency above the predetermined frequency of the filter 428, any noise being generated by the RF generator 22 and/or during the amplification process by the RF amplifier 24 that might lie below the predetermined frequency is effectively blocked. Consequently, the generation of any noise while generating RF signals to generate heat energy will not result in this noise being communicated or received by the MR/NMR receiving subsystem 500.

The MR/NMR receiving subsystem 500 includes the MRI RF and preamplifier circuitry 502 associated with the reception and processing of the MR/NMR signals received by the MRIH guide wire 440 as well as the matching/tuning and coupling circuitry 504 that comprises any of a number of circuits/circuit arrangements known to those skilled in the RF and MR/NMR arts that are appropriate for facilitating the coupling of the received MR/NMR signals from a MR receiver antenna to the MRI RF and preamplifier circuitry 502.

The MR/NMR receiving subsystem 500 also includes a filter 506 that is any of a number of filtering mechanisms known to those skilled in the RF and MR/NMR arts, that allows frequencies below a predetermined frequency to pass therethrough and blocks the transmission of frequencies that are above than the predetermined frequency and in more specific embodiments, the filter 428 is a low pass type of filter. In preferred embodiments, the predetermined frequency for the filter 428 is established so the RF signals being inputted into the MRIH guide wire 440 to generate heat energy are blocked and thus do not pass through with the MR/NMR signals being detected by the MRIH guide wire 440. In exemplary embodiments, the filter 506 is configured and arranged so that the predetermined frequency of the filter 506 is set so as to be above the frequency of the signals that would be detected during the MR/NMR imaging process. In particular exemplary embodiments, the MRI receiving filter 506 is configured and arranged so as to pass RF signals having a frequency less than about 1 GHz, more particularly a frequency less than about 500 MHZ, yet more particularly a frequency in the range of 200 MHz$\leq$freq$\leq$500 MHz, more specifically a frequency less than about 200 MHz.

In this way, even in the case where the RF power source 20 is generating RF signals to generate heat energy, the MRIH guide wire 440 can detect MR/NMR signals and pass these signals to the MR/NMR receiving subsystem 500 without the RF generator signals becoming noise to the MR/NMR receiving subsystem. Consequently, the catheter system 400 of this embodiment can generate RF signals to generate heat energy for heating the tissue at the target site while concurrently using the MRIH guide wire 440 as a MR/NMR receiver antenna so as to detect MR/NMR signals. Thus, the catheter system 400 of this embodiment is capable of MR/NMR imaging of the tissues at, about or proximal the target site concurrent with the heating of the tissues at the target site. Further such a system also is capable of administering or delivering the therapeutic medium concurrent with MR/NMR imaging of the tissues at, about or proximal the target site and/or concurrent with the heating of the tissues at the target site.

As indicated above, the catheter systems 10, 400 or the present invention are configured and arranged so as to administer/deliver a therapeutic medium to the target tissues of a target site. As also indicated above the therapeutic medium can comprise a therapeutic agent or a therapeutic agent in combination with a contrast agent to facilitate the MR imaging of the therapeutic agent. In the present invention, therapeutic agent shall be understood to encompass or include, but are not limited to drugs, genes, nucleic acid molecules including encoding different types of nucleic acid molecules, an angiogenic factor, a growth factor, a chemotherapeutic agent, a radionuclide, a protein, a polypetide, a peptide, a viral protein, a lipid, an amphiphile, a nuclease inhibitor, a polymer, a toxin, a cell, and modified forms and combinations thereof that are used in therapeutic procedures in connection with the injury, insult, trauma or ischemia to the tissues or cells of the target site that is accessed via a lumen or body cavity of the mammalian body, more particularly a human body, more specifically, the vascular system of a human body.

The nucleic acid molecule is preferably provided in a nucleic acid delivery vehicle which is lipid-based, viral-based, or cell-based. More preferably, the vector comprises a gene operably linked to an expression control sequence. In one aspect, the nucleic acid molecule comprises a sequence encoding a polypeptide for preventing, correcting and/or normalizing an abnormal physiological response, such as a disease. Exemplary polypeptides include, but are not limited to, hirudin, tissue plasminogen activator, an anchored urokinase activator, a tissue inhibitor of metalloproteinase, proliferating cell nuclear antigen, an angiogenic factor, a tumor suppressor, a suicide gene and a neurotransmitter. The vector may comprise sequences to facilitate its delivery to, or expression in, a target cell. For example, the vector may comprise a marker gene (e.g., encoding a fluorescent protein) and/or an origin of replication for a host cell and/or target cell.

In the case where the therapeutic medium is being delivered and MR/NMR imaging is to be performed to track and observe the efficacy of such delivery, the therapeutic medium is a therapeutic composition that includes a therapeutic agent as hereinabove described and a magnetic resonance imaging contrast agent.

MRI contrast agents primarily act by affecting T1 or T2 relaxation of water protons. Most MRI contrast agents generally shorten T1 and/or T2. When contrast agents shorten T1, this increases signal intensity on T1 weighted images. When contrast agents shorten T2, this decreases signal intensity particularly on T2 weighted pulse sequences. Thus, preferably, contrast agents used in the invention have adequate nuclear or relaxation properties for imaging that are different from the corresponding properties of the cells/tissue being imaged. Suitable contrast agents include an imageable nucleus (such as $^{19}$F), radionuclides, diamagnetic, paramagnetic, ferromagnetic, superparamagnetic substances, and the like. In a preferred aspect, iron-based or gadilinium-based contrast agents are used. Iron-based agents include iron oxides, ferric iron, ferric ammonium citrate and the like. Gadolinium based contrast agents include diethylenetriaminepentaacetic (gadolinium-DTPA). Manganese paramagnetic substances also can be used. Typical commercial MRI contrast agents include Omniscan, Magnevist (Nycomed Salutar, Inc.), and ProHance.

In one preferred embodiment, gadolinium is used as the MRI contrast agent. Less than about 28.14 mg/mL gadolinium (such as less than 6% Magnevist) is an adequate concentration for imaging and is minimally destructive of nucleic acid delivery vehicles. However, it is well within the skill of those in the art to vary and optimize the amount of contrast agent to add to the compositions depending on the nature of the contrast agent (e.g., their osmotic effects) and the length of time during which a target cell is exposed.

In other embodiments, the composition comprises a pharmaceutically acceptable carrier. Preferably, the carrier is non-toxic, isotonic, hypotonic or weakly hypertonic and has a relatively low ionic strength (e.g., such as a sucrose solution). Furthermore, it may contain any relevant solvents, aqueous or partly aqueous liquid carriers comprising sterile, pyrogen-free water, dispersion media, coatings, and equivalents, or diluents (e.g. Tris-HCl, acetate, phosphate), emulsifiers, solubilizers and/or adjuvants. The pH of the pharmaceutical preparation is suitably adjusted and buffered in order to be appropriate for use in humans or animals. Representative examples of carriers or diluents for an injectable—composition include water or isotonic saline solutions which are preferably buffered at a physiological pH (e.g., such as phosphate buffered saline, Tris buffered saline, mannitol, dextrose, glycerol containing or not polypeptides or proteins such as human serum albumin). The compositions also can comprise one or more accessory molecules for facilitating the introduction of a nucleic acid delivery vector into a cell and/or for enhancing a particular therapeutic effect.

The foregoing is illustrative and shall not be considered limiting as to the drugs or therapeutic compounds or agents, carriers, and accessory molecules that can be used to comprise the therapeutic medium of the present invention. Applicants also herein incorporate by reference the teachings and disclosures in their entirety of pending U.S. application U.S. Ser. No. 10/116,708 entitled Imaging Nucleic Acid Delivery and in particular those teachings and disclosures of the various therapeutic agents described therein.

Figure 5:
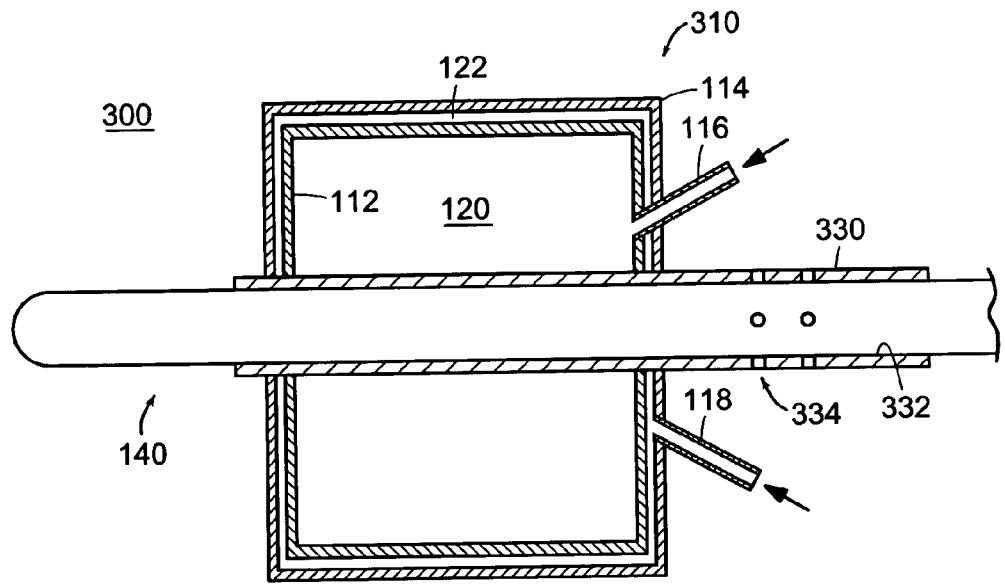
FIG. 5 is a cross-section view of a therapeutic delivery device according to yet another embodiment of the present invention.

Referring now to FIG. 5, there is shown a therapeutic delivery device 300 according to another embodiment of the present invention which therapeutic delivery device includes a housing 310 and a heating guide wire 140. As indicated above, such a therapeutic delivery device also can include a MRIH guide wire 440. The housing 310 comprises a balloon member 112, a flexible porous outer member 114 that is disposed generally about the balloon member, a channel member 330. The channel member 330 includes one or more perfusion through apertures or lumens 332. Reference shall be made to the heating guide wire 140, the balloon member 112, the flexible outer member 114, the input ports 116, 118 for the balloon member and the flexible outer member, the second channel 122, the channel member 130 and the heating guide wire for details not otherwise described hereinafter.

The one or more perfusion lumens 334 are arranged in the channel member 330 so as to extend substantially radially from the channel member lumen 332 to the outer surface of the channel member. More particularly, the perfusion lumens 334 are disposed and arranged within the channel member so as to be located on the proximal end of the housing 310. Each of the perfusion lumens 334 are configured and arranged so as to allow the biological fluid, such as blood, in the cavity/lumen/vessel being accessed that is blocked otherwise blocked by the therapeutic device 300, to flow through the lumen 332 of the channel member 330 and via the one or more perfusion lumens channels. In this way, the administration or delivery of the therapeutic medium as well as heating of the tissues at the target site can be done without interruption that would be occasioned by temporary deflation of the balloon member or other action to temporarily re-establish flow of the biological fluid in the cavity/lumen/vessel being accessed. In more particular embodiments, the housing 310 includes a plurality of perfusion lumens 334 and the lumen for each of the one or more, or the plurality of, perfusion lumens 334 is about 100 to about 500 µm in diameter.

Figures 6, 7:
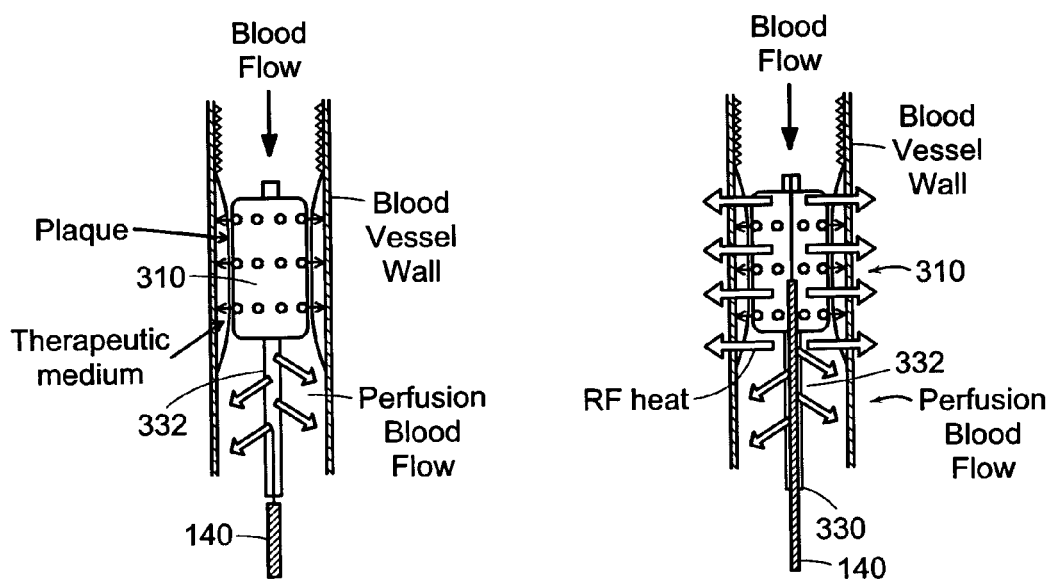
FIG. 6 is a schematic view of a blood vessel proximal a target site illustrating full perfusion flow with the therapeutic delivery device of FIG. 5.
FIG. 7 is a schematic view of a blood vessel proximal a target site illustrating RF heating with the therapeutic delivery device of FIG. 5.

Now with reference also to FIGS. 6-7, there is shown schematic views of a blood vessel to illustrate the flowing of the biological fluid with use of the therapeutic delivery device 300 of FIG. 5. As shown in FIG. 5, when full perfusion flow of biological fluid is desired, the user manipulates the heated guide wire 140 so as to partially withdraw it from the channel member so the substantially thicker portion of the heated guide wire 140 is withdrawn a sufficient distance so as to put at least one of the one or more perfusion lumens 334, more particularly each of the one or more perfusion lumens in full fluid communication with the axially extending lumen 332 of the channel member 330. In this way, the biological fluid (e.g., blood) upstream of the therapeutic delivery device 310 can pass through the channel member lumen 332 and thence through the one or more channel member perfusion lumens 334 to the downstream side of the therapeutic delivery device. As a result, flow of the biological fluid is established even though the balloon member 112 of the therapeutic delivery device remains in its inflated state. Further, it is with the scope of the present invention for the delivery/administering of the therapeutic medium to continue or occur while the biological fluid is flowing through the therapeutic delivery device. It should be recognized that it is well within the knowledge of those skilled in the art to determine how often and when to partially withdraw the heated guide wire 140 to obtain such full perfusion flow of the biological fluid.

As shown in FIG. 6, the differential pressure between the upstream and downstream sides of the therapeutic delivery device 310, can be such as to cause the biological fluid (e.g., blood) to flow about the heated guide wire 140 in the channel member lumen 332 and to be communicated to at least one of the perfusion lumens 334. Thus, at least some of the biological fluid (e.g., blood) can continue to be supplied to the blood vessel on the downstream side of the therapeutic delivery device even in the case where the heated guide wire is generating and distributing thermal energy (i.e., RF heat) to the tissues at the target site. It should be recognized that it is within the scope of the present invention for the heated guide wire 140 and/or the inner surface of the channel member lumen 332 to further include one or more surface artifacts (e.g., axially extending grooves or depressions) that facilitate the flow of biological fluid while maintaining good thermal contact between the channel member and the heated guide wire for distribution of thermal or heat energy to the tissues of the target site.

It should be recognized that it is well within the knowledge of those skilled in the art to determine how often and when to partially withdraw the heated guide wire 140 or MRIH guide wire 440 to obtain such full perfusion flow of the biological fluid.

Figure 8:
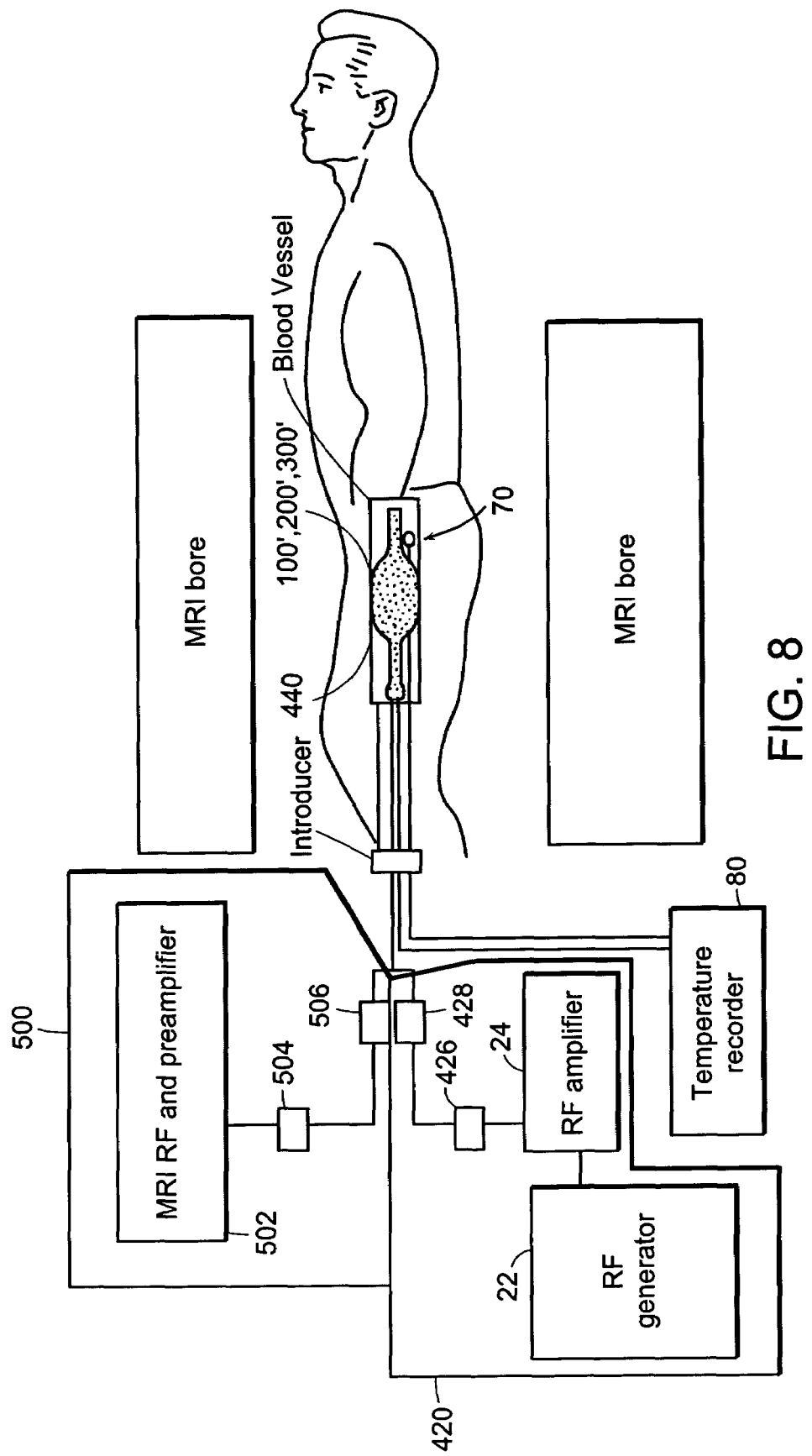
FIG. 8 is a schematic block diagram view to illustrate positioning and heating of target tissue of a blood vessel using the catheter system of FIG. 4.

The methodology of the present invention as to heating, administering/delivering the therapeutic medium and MR/NMR imaging can be best understood from the following discussion in conjunction with FIG. 8. It should be recognized that while the catheter system of FIG. 4 is illustrated this shall not be construed as limiting the methodology of the present invention to the illustrated system. In use, before the catheter/delivery device 100', 200' of the present invention is inserted into the body, and using known MR/NMR techniques an image of the volume to be treated as well as the region(s) to be traversed by the delivery device are initially acquired to develop baseline images for tracking. Using known techniques, the medical personnel or user accesses the body cavity, vessel lumen, vascular system and the like that is used to access the target site. After accessing this body structure, the medical personnel insert the therapeutic delivery device 100', 200' into the lumen used to traverse the body to the target site of the body cavity, vessel and the like to be treated.

Using known techniques for manipulating catheters, for example, the medical personnel manipulate the therapeutic delivery device 100', 200', 300' within the body lumen (e.g., vascular structure) until the housing 110, 210, 310 of the therapeutic delivery device is disposed or localized proximal the target site. Such manipulation and localizing is accomplished using any of a number of techniques known to those skilled in the art for monitoring and tracking the therapeutic deliver device, including MR/NMR imaging techniques and optical viewing as well as techniques using gamma or x-rays.

In the case of MR/NMR imaging the patient is typically disposed upon a moving platform that is moveable within the bore of the main field magnet, as hereinafter described. The MR/NMR images are acquired using any one of a number of techniques including use of imaging coils external to the body (see FIG. 9) and/or the MR!NMR loopless antenna formed by a MRIH guide wire 440 that is disposed within the therapeutic delivery device.

After localizing the therapeutic delivery device 100', 200', 300' to the target site, the medical personnel typically verify such localization using an appropriate imaging technique such as an MR/NMR imaging technique. In any event after completing such localization, the balloon member 112 of the therapeutic delivery device 100, 200, 300 is inflated by admitting a fluid such as warm saline into the first region 120. The fluid is continued to be admitted until the flexible outer member 114 comes into contact with the surface of the target site tissues.

After contacting and engaging the tissues, the heated guide wire or MRIH guide wire 440 is also located with respect to the surface of the target site tissues. In more particular embodiments, the MRIH guide wire 440 is localized about the midpoint of the housing and thus also should be located at about the centerline or midpoint of the lumen in which the therapeutic delivery device is located. As herein described, the medical personnel coordinate activation of the RF power source 420 and the administration/delivery of the therapeutic medium so that the tissues of the target site are heated and the therapeutic medium is delivered in the planned manner.

As illustration, the medical personnel activate the RF power source 420 prior to administering the therapeutic medium so as to raise the temperature of the target tissues to a desired value. This can be determined using MR thermometry, optical thermal sensors or any of a number of other sensing devices or techniques known to those skilled in the art. After the target tissues are so heated, the medical personnel inject the therapeutic medium into the second region 122 so that the therapeutic medium is distributed to the target site tissues/target cells via the porous flexible outer member 114 as hereinabove described. The injection process is continued until for example the desired amount of therapeutic medium is delivered. In the case where the therapeutic medium is a therapeutic composition including a MR/NMR contrast agent as well as the therapeutic agent, the medical personnel can MR/NMR image the target tissues and the movement of the therapeutic medium. It should be recognized that such imaging can be accomplished using the MRIH guide wire 440 as a loopless MR/NMR antenna even while heat energy is being generates and being distributed from the MRIH guide wire.

After distributing the therapeutic medium, the medical personnel de-activate the RF power source 420 and the therapeutic delivery device and the target tissues begin to cool down. Thereafter, and using techniques known to those skilled in the catheter and MR/NMR arts, the balloon member 112 is deflated and the therapeutic delivery device 100', 200', 300' is withdrawn from the body.

Figure 9:
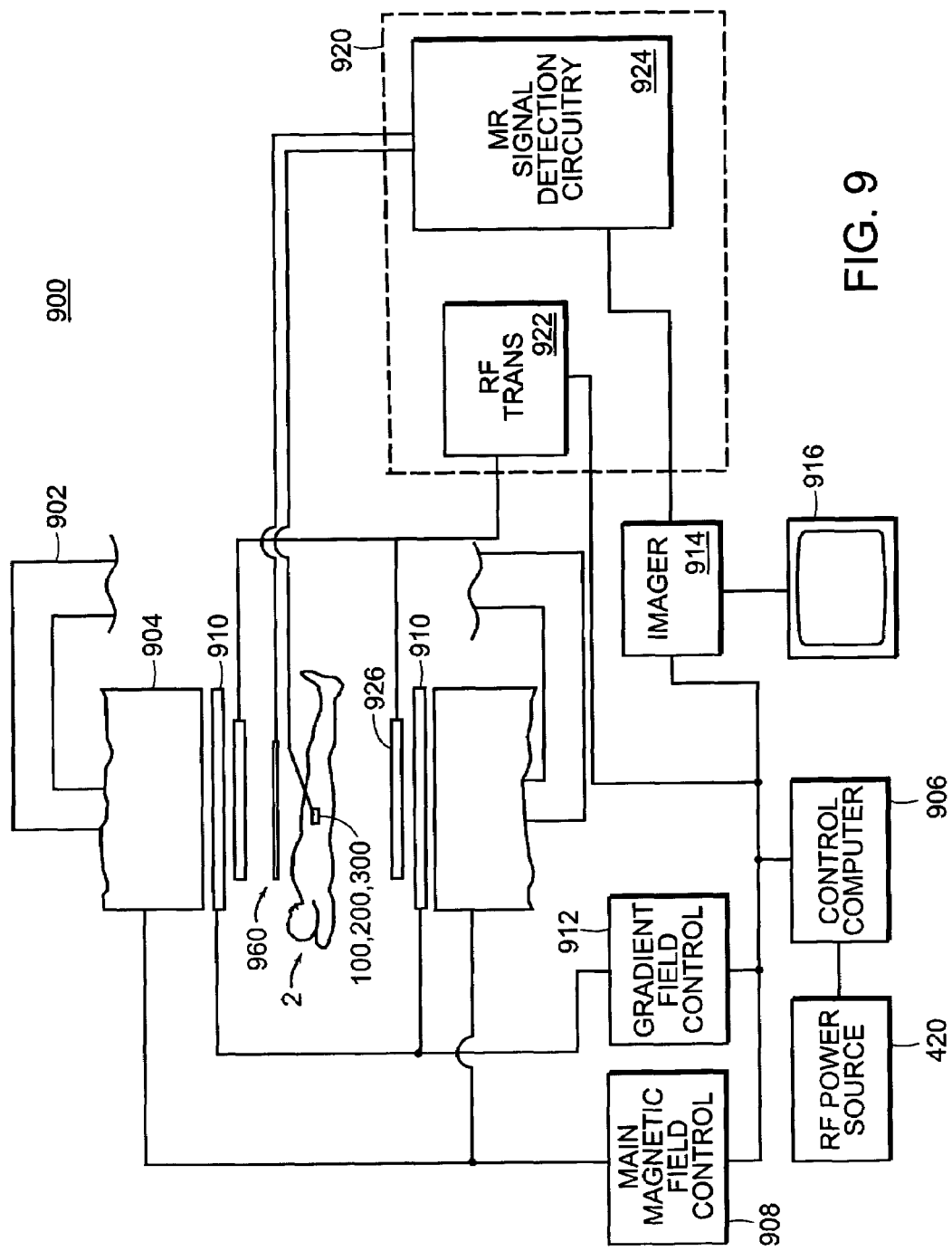
FIG. 9 is a schematic view of an exemplary magnetic resonance imaging (MRI) system having MR signal detection apparatus for use with a therapeutic delivery device an RF excitation according to the present invention.

Referring now to FIG. 9 there is shown a schematic view of an exemplary MRI system 900 having a RF excitation and MR signal detection apparatus 920 embodying a catheter system 400 according to the present invention. Although the RF excitation and MR signal detection apparatus 500 is referred to in the illustrated embodiment, this shall not comprise a limitation and other RF excitation and MR signal detection apparatus in accordance with the teachings of the present invention are contemplated for use in such an MRI system. Additionally, although a MRI system having a main magnet comprising a C-type magnet is illustrated, this also shall not constitute a limitation as it is with the contemplated scope of the present invention to adapt any of a number of known MRI magnets including superconducting magnet systems so as to be capable of using the RF excitation and MR signal detection apparatus of the present invention. Other exemplary MRI magnet systems are found in U.S. Pat. No. 4,689,563, the teachings of which are incorporated herein by reference.

Magnetic resonance imaging (MRI) is a technique that is capable of providing three-dimensional imaging of an object. A conventional MRI system typically includes a main or primary magnet that provides the main static magnetic field Bo, magnetic field gradient coils and radio frequency (RF) coils, which are used for spatial encoding, exciting and detecting the nuclei for imaging. Typically, the main magnet is designed to provide a homogeneous magnetic field in an internal region within the main magnet, for example, in the air space of a large central bore of a solenoid or in the air gap between the magnetic pole plates of a C-type magnet. The patient or object to be imaged is positioned in the homogeneous field region located in such air space. The gradient field and the RF coils are typically located external to the patient or object to be imaged and inside the geometry of the main or primary magnet(s) surrounding the air space. There is shown in U.S. Pat. Nos. 4,689,563; 4,968,937 and 5,990,681, the teachings of which are incorporated herein by reference, some exemplary MRI systems.

In MRI, the uniform magnetic field $B_o$ generated by the main magnet is applied to an imaged object by convention along the Z-axis of a Cartesian coordinate system, the origin of which is within the imaged object. The uniform magnetic field $B_o$ being applied has the effect of aligning the magnetization arising from the nuclei of the atoms comprising the imaged object, along the Z-axis, such nuclei possess a nuclear magnetization due to their having an odd number of protons or neutrons. In response to RF magnetic field pulses of the proper frequency, with field direction orientated within the XY plane, the nuclei resonate at their Larmor frequencies, $\omega=\gamma B_o$ where $\gamma$ is called the gyromagnetic ratio. In a typical planar imaging sequence, the RF signal centered about the desired Larmor frequency is applied to the imaged object at the same time a magnetic field gradient $G_z$ is being applied along the Z-axis. This gradient field $G_z$ causes only the nuclei in a slice of limited thickness through the object perpendicular to the Z-axis, to satisfy the resonant condition and thus be excited into resonance.

After excitation of the nuclei in the slice, magnetic field gradients are applied along the X- and Y-axes respectively. The gradient $G_x$ along the X-axis causes the nuclei to precess at different frequencies depending on their position along the X-axis, that is, $G_x$ spatially encodes the precessing nuclei by frequency. Thus, this gradient is often referred to as a frequency encoding or read-out gradient. The Y-axis gradient $G_y$ is incremented through a series of values and encodes the Y position into the rate of change of the phase of the processing nuclei as a function of gradient amplitude, a process typically referred to as phase encoding.

The MRI system 900 includes an electromagnet 902, a computer 906, a main magnetic field control 908, a gradient coil sub-system 910, gradient magnetic field power amplifiers 912, an imager 914, a display device 916 and a RF excitation and MR signal detection apparatus 920 according to the present invention.

The electromagnet 902 produces a strong main magnetic field Bo in which a body 2 to be imaged, a patient, is placed on a suitable support or table (not shown). The strength of the magnetic field in the gap between the pole pieces 904, and hence in the body 2, is controlled by a computer 906 via a main magnetic field control 908, which controls the supply of energizing current to the electromagnet energizing coil. Alternatively, for superconducting MRI electromagnets, with inherently highly-stable fields, the field is charged and set to an exact value upon installation, and not altered during normal operation.

The gradient coil sub-system 910, comprising one or more gradient coils, whereby a magnetic field gradient can be imposed on the static magnetic field in the sample volume in any one or more of three orthogonal directions X, Y, and Z. The gradient coil sub-system 910 is energized by a gradient field power amplifiers 912 that are under the control of the computer.

The RF excitation and MR signal detection apparatus 920 according to the present invention includes an RF transmitter 922, MR signal detection circuitry 924, transmitter coils 926, the MRIH guide wire 440 of the therapeutic delivery device 100', 200', 300' of the present invention forming a loopless MR/NMR antenna and other coils or MR antennas 960. The RF transmitter 922 is under the control of the computer 906 so that RF field pulses or signals are selectively generated and applied to the body transmit coil for excitation of magnetic resonance in the body. It should be recognized that the computer 906 also can be configured and arranged so as to comprise the RF power source controller 26 and to also control the RF power source and when and for how long thermal energy is to be supplied to the tissues of the target site.

While these RF excitation pulses are being applied to the body, T/R switches of the MR signal detection circuitry 924 are actuated so as to de-couple the MR/NMR signal detection coils 960 and loopless MR/NMR antenna 440 from the MR signal detection circuitry. Following application of the RF excitation pulses, the T/R switches are again actuated to couple the MR/NMR signal detection coils and/or antennas to the MR signal detection circuitry 924.

The MR/NMR coils 960 or antennas external to the body detect or sense the MR signals resulting from the excited nuclei in the body and conducts the MR signals onto the MR signal detection circuitry 924 (e.g., the receivers/preamplifiers thereof). Similarly, the loopless MR/NMR antenna comprised by the MRIH guide wire 440 detect or sense the MR signals resulting from the excited nuclei in the body and proximal the MRIH guide wire and conducts the MR signals onto the MR signal detection circuitry 924 (e.g., the receivers/preamplifiers thereof). In an exemplary embodiment, the MR signal detection circuitry 924 includes a multi-channel receiving device and the signals from each of the coils and/or antennas are provided to a different channel thereof. These detected MR signals are in turn passed onto the imager 914. The imager 914, under the control of the computer 906, processes the signals to produce signals representing an image of a region of interest in the body 2. These processed signals are sent onto a display device 516 to provide a visual display of the image.

In operation, the uniform magnetic field $B_o$ generated by the main magnet 902 is applied to the body 2 by convention along the Z-axis of a Cartesian coordinate system, the origin of which is at the center of the magnet and typically near or within the region of interest being imaged in the object. The uniform magnetic field $B_o$ being applied has the effect of aligning the nuclear magnetization of the nuclei in the body 2, along the Z-axis. In response to RF pulses of the proper frequency being generated by the RF transmitter 922, that are orientated within the XY plane, the nuclei resonate at their Larmor frequencies, producing a time-dependent XY magnetization at the NMR frequency which can be detected by a coil or antenna. In one typical imaging sequence, the RF signal centered about the desired Larmor frequency is applied to the body 2 at the same time a magnetic field gradient $G_z$ is being applied along the Z-axis by means of the gradient control sub-system 910. This gradient field $G_z$ causes only the nuclei in a slice with a limited width through the body 2 along the XY plane, to have the resonant frequency and to be excited into resonance, a process typically referred to as selective excitation.

After excitation of the nuclei in the slice, magnetic field gradients are applied along the X- and Y-axes respectively. The gradient $G_x$ along the X-axis causes the nuclei to precess at different frequencies depending on their position along the X-axis, that is, $G_x$ spatially encodes the precessing nuclei by frequency (i.e., frequency encoding). The Y-axis gradient $G_y$ is incremented through a series of values and encodes the Y position into the rate of change of the phase of the precessing nuclei as a function of gradient amplitude, a process typically referred to as phase encoding. Phase-encoding can be extended to more than one dimensions for example, by replacing selective excitation of the single slice using a $G_x$ gradient pulse applied during excitation as described above, with Z-gradient incrementation after the excitation. By such means full three-dimensional (3D) volume imaging is achieved, for example, by phase-encoding in two dimensions (Z, Y) and applying frequency encoding in the third dimension (X).

EXAMPLE #1

A study was undertaken to demonstrates the use the magnetic resonance imaging guidewire (MRIG) as a multi-functional device, not only as a receiver antenna to generate intravascular high-resolution MR images of atherosclerotic plaques and as a conventional guidewire to guide endovascular interventions under MR imaging, but also as an intravascular heating source to produce local heat for thermal enhancement of vascular gene transfection. More particularly, this study focused on the use of a clinical size, 0.032-inch diameter MRIG as an intravascular heating source to deliver controlled thermal energy from an external microwave generator into the target vessels for the enhancement of catheter-based vascular gene transfection.

A clinical size, 0.032-inch diameter MR imaging-guidewire was used which has been successfully used to generate intravascular high-resolution MR images of the atherosclerotic vessel wall and for guidance of vascular interventions under MR imaging. The MRIG was a loopless antenna, which consisted of an 8-cm long conducting wire that was an extended inner conductor from a 25-inch long coaxial cable. The inner conductor of the MRIG consisted of a gold-plated nitinol wire with a radius of 0.1 mm. The dielectric was polytetrafluoroethylene ($\epsilon_r=2$) and had a radius of 0.33 mm. The outer conductor consisted of nitinol ($\sigma=1\times10^6$ S/m) with a radius of 0.42 mm. The MRIG was connected either to an external 2.45 GHz microwave generator (Opthos Instruments, Rockville, Md.) for heating, or connected to an MR scanner for imaging.

A New Zealand white rabbit, approximately 5 kg in weight, with the aorta approximately 6 mm in diameter was used to investigate the use of an MRIG to deliver microwave power to the vessel and to establish a heating protocol for the enhancement of vascular gene transfection in vivo. All animals were treated according to the "Principles of Laboratory Animal Care" of the National Society for Medical Research and the "Guide for the Care and Use of Laboratory Animals" (NIH Publication No. 80-23, revised 1985). The Animal Care and Use Committee at our institution approved the experimental protocol.

Figure 10:
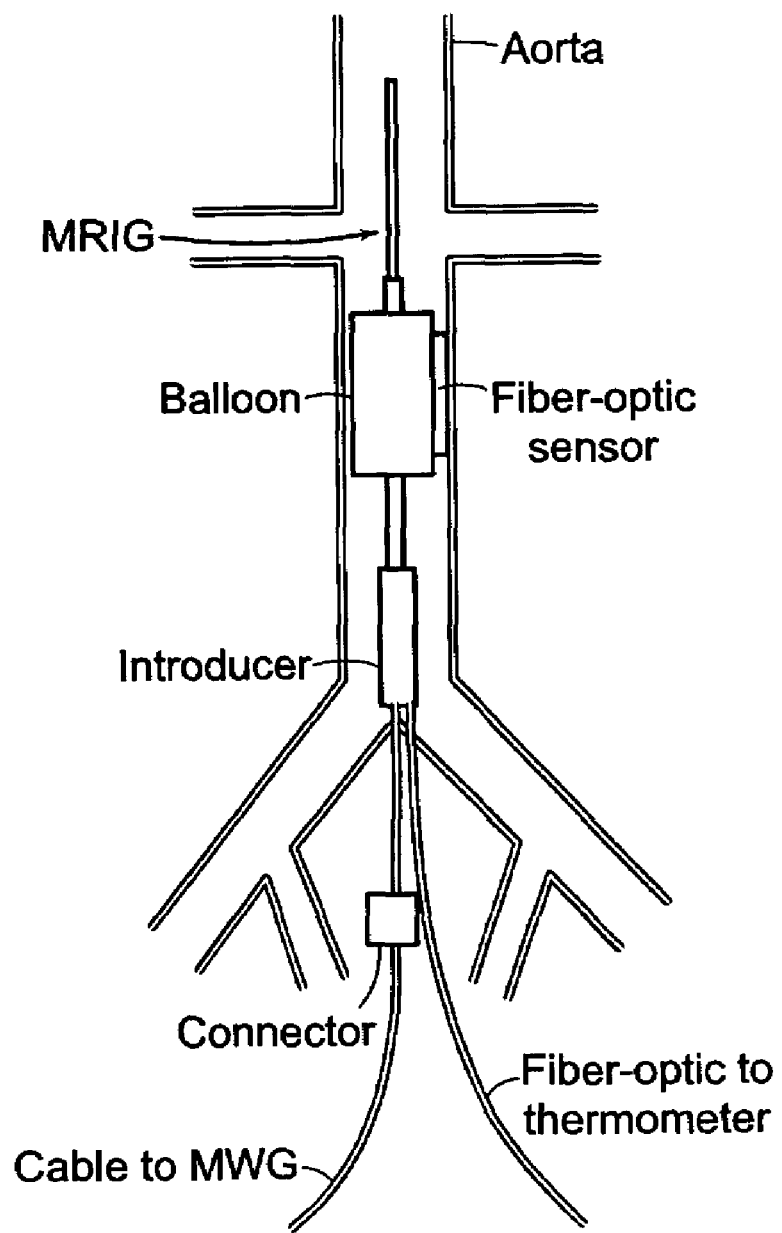
FIG. 10 is a schematic view of the invivo experimental setup in a rabbit aorta.

Through a laparotomy, a 5F balloon catheter with a balloon portion of 6 mm in diameter and 2 cm in length (Boston Scientific, Boston, Mass.), and a 0.6-mm fiber-optic temperature sensor (FISO Technologies, Ste-Foy, Quebec, Canada) were positioned into the lower abdominal aorta at a level 2 cm below the renal arteries as shown in FIG. 10. The sensor portion of the fiber-optic probe was attached side-by-side onto the balloon. Thus, inflation of the balloon with 37° C. saline propelled the fiber-optic probe against the arterial wall.

The MRIG was placed into the balloon catheter, so that the active imaging/heating region of the MRIG was positioned in the center of the balloon. The MRIG was connected to an external 2.45 GHz microwave generator, and the fiber-optic sensor was connected to a digital thermometer (FISO Technologies, Canada). Subsequently, the microwave generator was operated, at different power levels from 2 to 24 watts (W), to deliver thermal energy to the MRIG. The steady-state temperature increases after several seconds were recorded using a digital thermometer. The heating experiments were repeated in triplicate.

In the experimental setting, the target vessel wall was locally heated during mechanical compression by the inflated balloon. The mechanical compression facilitated the microwave heating-induced thermal damage on the balloon-stressed target vessel wall. The potential thermal damage in vivo from microwave heating/balloon compression was evaluated by examining the histological difference before and after microwave heating at the target in living animals. In addition, during the in vivo experiments, the possibility of simultaneously generating high-resolution MR images of the target vessels using the same heat-delivery MRIG was investigated with the inflated balloon in the same target vessel.

Six New Zealand white rabbits, approximately 5 kg in weight were used and using the same surgical method mentioned above, the 0.032-inch MRIG, along with the SF balloon and the 0.6-mm fiber-optic temperature sensor, were positioned into the aorta. Then, while inflating the balloon with saline, the targeted aorta was heated with the MRIG for 20 minutes by operating the microwave generator at 20-25 watts, which resulted in a temperature increase to 41° C. at the target aortic wall.

MR imaging was performed in a 1.5 Tesla MR scanner (GE Medical System, Milwaukee, Wis.). High-resolution axial and sagittal images were acquired with two pulse sequences: (i) T1-weighted imaging with an SE sequence of 500/11 ms TR/TE, 4 and 8-cm FOV, and 256×256 matrix; and (ii) T2-weighted imaging with an FSE sequence of 2000/100 ms TR/TE, 15.6-kHz bandwidth, 4 and 8-cm FOV, and 256×256 matrix. During MR imaging, the MRIG was connected to the MRI preamplifier and operated in the receive-only mode.

Immediately after the heating, the heat-targeted aorta and non-heated aorta (as a control) were harvested for histological examination. The specimens were embedded in paraffin, cut into 5-µm slices on a cross-sectional view, and stained with Masson Trichrome stain.

The pattern of simulated power distribution was found to be cylindrically symmetric, analogous to the geometry of vessels, and was localized to the target vessel area (FIG. 2). The calculated half-power heating length was 1.7 cm at the microwave frequency, which is close to the 2-cm length of the 5F catheter balloon. Although some microwave energy was lost through the MRIG during microwave energy transfer, the desired temperature of 41° C. was achieved at the target vessel wall in vivo.

Under MR imaging, the inflation/deflation of the balloon could be monitored. On T1- and T2-weighted MR images, the balloon-inflated target aortic wall also could be imaged at a resolution of 157 µm (FIG. 4).

Clinically, all rabbits survived during the experiments. Histopathologically, in both gross and microscopic examinations, there were no findings of thermal damages, such as vacuolization, coagulation, or carbonization. Also there was not found any evidence of possible mechanical injury to the vessel wall due to the insertion of the MRIG.

The study demonstrates the potential of using an MR imaging-guide wire as a multi-functional device for vascular gene therapy, not only as a receiver antenna to generate intravascular high-resolution MR imaging of the target vessel wall and as a conventional guide wire to guide endovascular interventions, but also as an intravascular local heating source to deliver controlled therapeutic heat into target vessels. The advantages of using the MRIG as an intravascular local heating source include (i) the thin MRIG can be easily positioned, via any endovascular interventional device, into a target vessel to generate local and axisymmetric heating at the target; (ii) the MRIG produces a power distribution that is cylindrically symmetric and analogous to the geometry of vessels and localized to the target vessel area; and (iii) the MRIG can be used as a multi-functional device to simultaneously generate imaging and heating at the target vessels, and thermal power input through the MRIG can be easily controlled at the external microwave generator. In addition, it should be greatly beneficial to combine MR thermal mapping techniques with the current design, to monitor and control the location, distribution, and extent of the delivered therapeutic heat at the target vessels under MR imaging.

EXAMPLE #2

An MR-imaging/radiofrequency (RF)-heating system was used to determine the feasibility for enhancement of vascular gene transduction in vivo. Green fluorescent protein (GFP) gene/lentivirus was transferred into the bilateral femoral artery walls of 7 pigs via a catheter-based delivery. During and after infusion of GFP/lentivirus, the targeted right femoral arteries were heated from 37° C. to 41° C. using the MR-imaging/RF-heating system. Quantitative Western Blot analysis of harvested vessels showed that GFP expression was significantly higher in the heated group than in the non-heated group.

The right carotid arteries of anesthetized domestic pigs were cannulated with 7F introducers. Based on an X-ray angiogram of the pelvic artery tree, a 5F Remedy gene delivery balloon catheter was inserted into the left femoral artery. The catheter was composed of an angioplasty balloon, which was surrounded by multiple gene infusion channels with many micropores on the surface. After inflation of the balloon with a saline/contrast agent mixture, 1.5-ml GFP/lentivirus solution was infused into the target vessel wall at an infusion flow of 10 ml/hr.

The balloon catheter was re-positioned into the right femoral artery and a 0.014-inch MR imaging-guidewire (MRIG) placed into the guidewire channel of the catheter, with the hot-spot of the MRIG in the middle of the balloon. The MRIG was then connected to the MR-imaging/RF-heating system. Subsequently, GFP/lentivirus was transferred into the arterial wall using the same infusion protocol described above, while 180 MHz RF, operated at 4-watt output power, was delivered via the MRIG into the target vessel during and after infusion for 20 minutes. A temperature increase from 37° C. to 41° C. was previously confirmed using this heating protocol. At day 6 after infusion, the pigs were sacrificed and the bilateral target vessels were harvested for quantitative Western Blot analysis.

Gene delivery procedures with RF-heating in all pigs were successful. All seven pigs transduced with GFP/lentivirus survived with no clinical abnormalities. GFPs were expressed in all cases, with a 4.7-fold higher GFP gene expression in the heated arteries than in the non-heated arteries (P=0.026, paired t-test, n=7).

EXAMPLE #3

An MR imaging-guide wire (MRIG) was used to conduct microwave (MW) heating during green fluorescent protein (GFP) gene-lentiviral transduction in human vascular smooth muscle cell (SMC) phantoms to evaluate the effect of heating on the enhancement of vascular gene transduction. The purpose was to evaluate the use of an MR imaging-guide wire (MRIG) as a vehicle to deliver external thermal energy into cell culture phantoms for the enhancement of gene transduction expression in human vascular smooth muscle cells (SMC).

A four-chamber, cell culture slide was placed on a 37° C. water surface in a heating bath. The "hot spot" of an MR imaging-guide wire, 0.047 inch in diameter, was attached under the bottom of one end-chamber of the slide, and the MRIG was connected to an external 2.45 GHz microwave (MW) generator (Opthos, Rochville, Md.). Four fiber-optic probes were then attached on the bottoms of four chambers of the slide. During heating, temperature increase in each chamber was recorded using a multi-channel, digital thermometer (Fiso, Quebec, Canada). The MRIG-attached chamber was heated from 37° C. to 40-41° C.

Human arterial SMCs (Clonetics, San Diego, Calif.) were cultured in the four chambers of the slide at a concentration of 10,000 cells per chamber and then incubated at 37° C. for 24 hours to produce the GFP- lentiviral vector used for gene transduction.

Before transduction, the SMC layer on the bottom of the MRIG-attached chamber was heated by MW at 40° C. for 15 minutes. Then, the SMCs in the four chambers were transduced with GFP-lentivirus for 15 minutes using a protocol provided by Life Technologies, Inc. (Rockville, Md.). The desired temperature increase to 40-41° C. at the bottom of the MRIG-attached chamber was achieved with an MW output power of 24-26 watts. The temperature increase was reduced as the distance increased between the chamber and the MRIG.

During the transduction, the MRIG-attached chamber bottom was constantly heated at 40-41° C. After heating, the untransducted GFP-lentiviral vectors were removed by washing the chambers three times with the SmGM-2 culture medium. Then, the SMCs were further incubated for 5 days to allow sufficient GFP expression. At day 6, a confocal microscopy was used to calculate and compare GFP transduction rates among the four-chamber cell groups using cell-plating efficiencies in triplicate.

The GFP transduction rate was the highest at 41° C. (75.6%), followed by 38° C. (32.1%), and the lowest at 37° C. (17.2%). These results were also confirmed by confocal microscopic correlations. More particularly, the results showed that the transduction rate at 41° C. was 4.4-fold higher than that at 37° C.

In sum, the investigation showed that gene transduction in vascular SMCs can be enhanced by microwave heating through an MR imaging-guide wire in vitro, which offers the potential to use the MRIG/MW system to intravascularly enhance vascular gene transduction in vivo.

Although a preferred embodiment of the invention has been described using specific terms, such description is for illustrative purposes only, and it is to be understood that changes and variations may be made without departing from the spirit or scope of the following claims.

What is claimed is:

1. A method for delivering a therapeutic medium to a target site of a vessel, said method comprising the steps of:
    positioning a thermal energy delivery and imaging device proximal to the target site;
    introducing the therapeutic medium to the target site over a predetermined time period;
    activating the thermal energy delivery and imaging device so as to heat the internal target site thereby locally increasing a temperature of tissue at the target site; and
    imaging the body using an MR/NMR imaging technique during said steps of introducing and activating the therapeutic medium;
    wherein said activating occurs before and during said step of introducing, and wherein the therapeutic medium includes a gene therapy agent.

2. The method of claim 1, wherein said steps of positioning includes:
    introducing a catheter that houses the thermal energy delivery device into one of a lumen or body cavity of a body; and
    manipulating the catheter so as to traverse the body lumen or body cavity and be positioned proximal the target site.

3. The method of claim 2, wherein the catheter includes a balloon member and wherein said step of positioning further includes the step of inflating the balloon member so as to at least locally position the thermal energy delivery device at desired position with respect to the target site.

4. The method of claim 3, wherein the target site is a vessel lumen and wherein said inflating includes inflating the balloon member so as to local position the thermal energy device so as to be generally located positioned a center of the vessel lumen.

5. The method of claim 1, wherein the target site includes a wall of a blood vessel of the body.

6. A method for delivering a therapeutic medium to a target site of a vessel, said method comprising the steps of:
    introducing a catheter that houses a thermal energy delivery and imaging device into one of a lumen or body cavity of a body;
    manipulating the catheter so as to traverse the body lumen or body cavity and so the thermal energy delivery and imaging device is positioned proximal the target site;
    activating the thermal energy delivery and imaging device so as to heat the internal target site thereby locally increasing a temperature of tissue at the target site,
    wherein said activating occurs:
    before and during introducing the therapeutic medium,
    introducing the therapeutic medium to the target site over a predetermined time period; and
    imaging the body using an MR/NMR imaging technique during said steps of manipulating, activating the thermal energy delivery and imaging device and introducing the therapeutic medium.

7. The method of claim 6, wherein said steps of imaging and activating are conducted at essentially the same time.

8. A method for delivering a therapeutic medium to a target site of a vessel, said method comprising the steps of:
    positioning a thermal energy delivery and imaging device proximal the target site;
    activating the thermal energy delivery and imaging device so as to heat the internal target site thereby locally increasing a temperature of tissue at the target site;
    wherein said activating occurs
    before and during introducing the therapeutic medium,
    introducing the therapeutic medium to the target site over a predetermined time period; and
    imaging the body using an MR/NMR imaging technique during said steps of positioning, activating and introducing the therapeutic medium;
    wherein the thermal energy delivery and imaging device is used to detect MR/NMR signals from the target site.

9. The method of claim 8, wherein said steps of positioning includes:
    introducing a catheter that houses the thermal energy delivery and imaging device into one of a lumen or body cavity of a body; and
    manipulating the catheter so as to traverse the body lumen or body cavity and so the thermal energy delivery and imaging device is positioned proximal the target site.

10. The method of claim 9, wherein the catheter includes a balloon member and said step of positioning further includes the step of inflating the balloon member so as to at least locally position the thermal energy delivery and imaging device at desired position with respect to the target site.

11. The method of claim 10, wherein the target site is a vessel lumen and wherein said inflating includes inflating the balloon member so as to local position the thermal energy and delivery device so as to be generally located positioned a center of the vessel lumen.

12. The method of claim 8, wherein the therapeutic medium further includes a contrast agent and wherein said imaging includes imaging the therapeutic medium including the contrast agent being introduced.

13. The method of claim 8, wherein the therapeutic medium includes a gene therapy agent.

14. The method of claim 8, wherein the target site includes a wall of a blood vessel of the body.

15. The method of claim 8, wherein a volume of tissue in which thermal energy is delivered during said step of activating is different than another volume of tissue being imaged during said step of imaging.

16. The method of claim 8, wherein fluid flows through the vessel and wherein the method further comprises the step of maintaining a flow of fluid through the vessel during said steps of positioning and activating.

17. The method of claim 16, further comprising the step of configuring the thermal energy delivery and imaging device so as to establish one or more flow paths that fluidly couple an upstream portion of the vessel that is upstream of the thermal energy delivery to a downstream portion of the vessel.

18. The method of claim 8, wherein the thermal energy delivery and imaging device includes a wire to generate the heat energy and to detecting MR/NMR signals and the method further comprises filtering signal outputs from the wire so as to exclude signals that are not in the frequency band(s) for the MR/NMR signals from being used for imaging.

19. The method of claim 8, wherein said steps of imaging and activating are conducted at essentially the same time.

20. A method for delivering a therapeutic medium to a target site of a vessel in which fluid flows, said method comprising the steps of:
positioning a thermal energy delivery and imaging device proximal the target site;
activating the thermal energy delivery and imaging device so as to heat the internal target site thereby locally increasing a temperature of tissue at the target site;
wherein said activating occurs
before and during introducing the therapeutic medium,
maintaining a flow of fluid through the vessel during said steps of activating and introducing the therapeutic medium; and
imaging the body using an MR/NMR imaging technique during said steps of positioning, activating the thermal energy delivery and imaging device and introducing the therapeutic medium;
wherein the thermal energy delivery and imaging device is used to detect MR/NMR signals from the target site.

21. The method of claim 20, further comprising the step of configuring the thermal energy delivery and imaging device so as to establish one or more flow paths that fluidly couple an upstream portion of the vessel that is upstream of the thermal energy delivery to a downstream portion of the vessel.

22. The method of claim 20, wherein said steps of positioning includes:
introducing a catheter that houses the thermal energy delivery and imaging device into one of a lumen or body cavity of a body; and
manipulating the catheter so as to traverse the body lumen or body cavity and so the thermal energy delivery and imaging device is positioned proximal the target site.

23. The method of claim 20, wherein the therapeutic medium includes a gene therapy agent.

24. The method of claim 22, wherein the catheter includes a balloon member and said step of positioning further includes the step of inflating the balloon member so as to at least locally position the thermal energy delivery and imaging device at desired position with respect to the target site.

25. The method of claim 24, wherein the target site is a vessel lumen and wherein said inflating includes inflating the balloon member so as to local position the thermal energy delivery and imaging device so as to be generally located positioned a center of the vessel lumen.

26. The method of claim 20, wherein the target site includes a wall of a blood vessel of the body.

27. The method of claim 20, further comprising the step of imaging the target site using an MR/NMR imaging technique at least during said step of activating the heat source and introducing the therapeutic medium.

28. The method of claim 27, wherein said imaging is conducted during said step of positioning.

29. The method of claim 27, wherein the therapeutic medium further includes a contrast agent and wherein said imaging includes imaging the therapeutic medium including the contrast agent being introduced.

30. The method of claim 27, wherein a volume of tissue in which thermal energy is delivered during said step of activating is different than another volume of tissue being imaged during said step of imaging.

31. The method of claim 27, further comprising the step of configuring the thermal energy delivery device so as to include an antenna for detecting MR/NMR signals and wherein said step of imaging is conducted during said steps of positioning, activating and introducing.

32. The method of claim 31, wherein the thermal energy delivery and imaging device includes a wire to generate the heat energy and to act as the antenna, and the method further comprises filtering signal outputs from the wire so as to exclude signals that are not in the frequency band(s) for the MR/NMR signals from being used for imaging.

33. The method of claim 27, wherein said steps of imaging and activating are conducted at essentially the same time.

* * * * *